(12) United States Patent
Pratt et al.

(10) Patent No.: US 7,029,501 B2
(45) Date of Patent: Apr. 18, 2006

(54) HAIR DYE COMPOSITION

(75) Inventors: Dominic Pratt, Darmstadt (DE); Toshio Kawagishi, Minamiashigara (JP)

(73) Assignees: Kao Corporation, Tokyo (JP); Fuji Photo Film, Co., Ltd., Minamiashigara (JP)

( * ) Notice: Subject to any disclaimer, the term of this patent is extended or adjusted under 35 U.S.C. 154(b) by 40 days.

(21) Appl. No.: 10/660,475

(22) Filed: Sep. 12, 2003

(65) Prior Publication Data
US 2004/0139560 A1 Jul. 22, 2004

(30) Foreign Application Priority Data
Sep. 13, 2002 (JP) .............................. 2002-269172

(51) Int. Cl.
*A61K 7/13* (2006.01)
(52) U.S. Cl. ..................... 8/405; 8/407; 8/409; 8/570; 8/688; 8/689; 8/691; 8/692; 548/37.1
(58) Field of Classification Search .................... 8/405, 8/407, 409, 570, 688, 689, 691, 692; 548/37.1
See application file for complete search history.

(56) References Cited

U.S. PATENT DOCUMENTS

| | | | | |
|---|---|---|---|---|
| 4,702,863 A | | 10/1987 | Bugaut et al. ............... | 861/396 |
| 5,344,933 A | * | 9/1994 | Mikoshiba et al. .......... | 544/282 |
| 5,931,973 A | | 8/1999 | Malle et al. .................... | 8/431 |
| 6,451,069 B1 | | 9/2002 | Matsunaga et al. ............ | 8/405 |

FOREIGN PATENT DOCUMENTS

| | | |
|---|---|---|
| EP | 1 240 891 | 9/2002 |
| JP | 3-83687 | 4/1991 |
| JP | 3-83688 | 4/1991 |
| JP | 3-83689 | 4/1991 |
| JP | 3-92386 | 4/1991 |
| JP | 5-202305 | 8/1993 |
| JP | 6-271435 | 9/1994 |
| JP | 2001-261535 | 9/2001 |

OTHER PUBLICATIONS

Patent Abstracts of Japan, JP 06-080900, Mar. 22, 1994.
E. Schröder, et al., Georg Thieme Verglag, Stuttgart, table 6, pp. 24-39, XP-002266407, "Arzeimitte L Chemie I", 1976.

* cited by examiner

*Primary Examiner*—Eisa Elhilo
(74) *Attorney, Agent, or Firm*—Oblon, Spivak, McClelland, Maier & Neustadt, P.C.

(57) ABSTRACT

Provided is a hair dye composition containing a dissociative direct dye represented by the following formula (1):

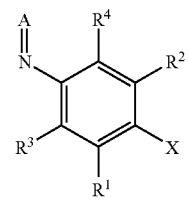

(1)

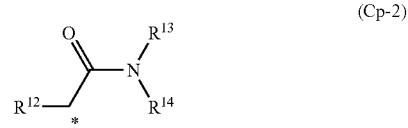

(Cp-1)

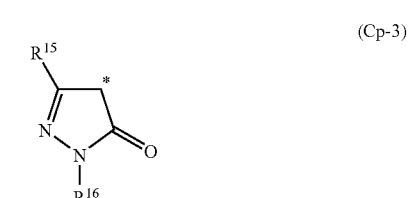

(Cp-2)

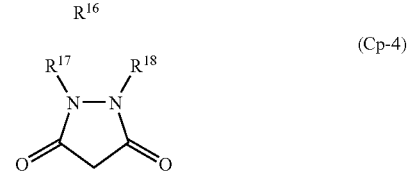

(Cp-3)

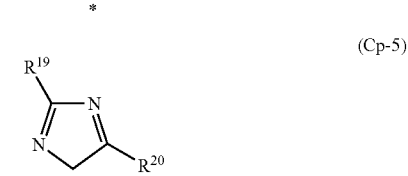

(Cp-4)

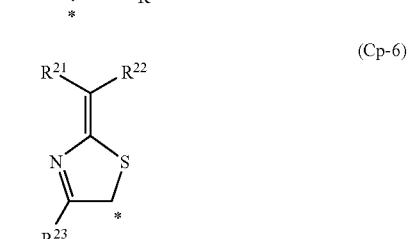

(Cp-5)

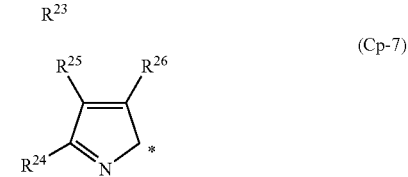

(Cp-6)

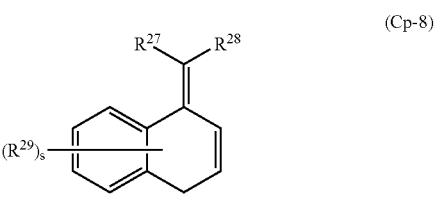

(Cp-7)

(Cp-8)

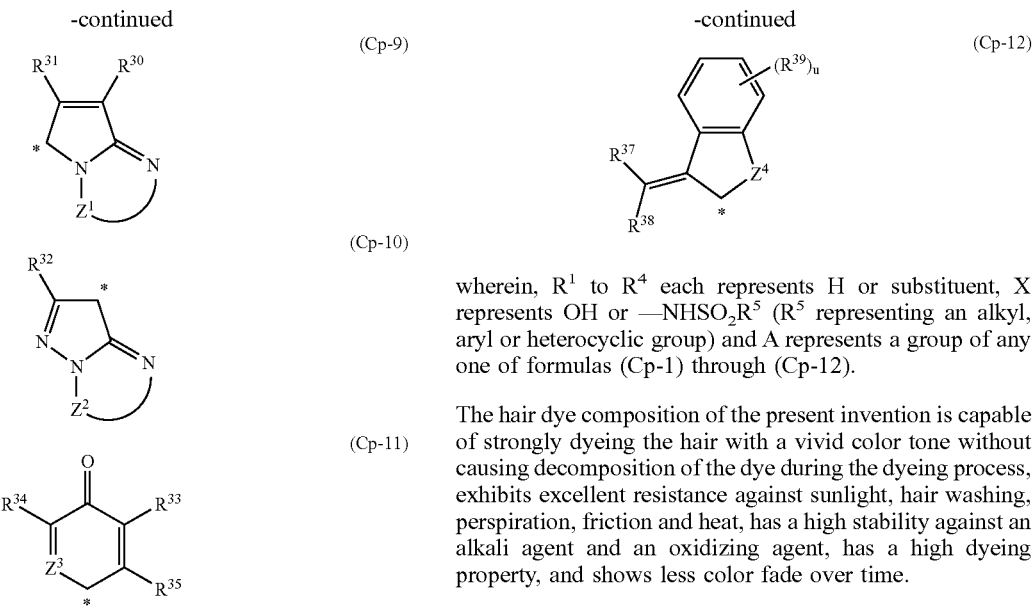

wherein, $R^1$ to $R^4$ each represents H or substituent, X represents OH or —$NHSO_2R^5$ ($R^5$ representing an alkyl, aryl or heterocyclic group) and A represents a group of any one of formulas (Cp-1) through (Cp-12).

The hair dye composition of the present invention is capable of strongly dyeing the hair with a vivid color tone without causing decomposition of the dye during the dyeing process, exhibits excellent resistance against sunlight, hair washing, perspiration, friction and heat, has a high stability against an alkali agent and an oxidizing agent, has a high dyeing property, and shows less color fade over time.

26 Claims, No Drawings

HAIR DYE COMPOSITION

BACKGROUND OF THE INVENTION

1. Field of the Invention

The present invention relates to a hair dye composition having excellent dyeing power, being capable of imparting a wide range of colors to the hair without losing their vividness, and showing less color fade over time.

2. Background Art

Hair dyes can be classified by a dye to be used therefor, or by whether they have bleaching action of melanin or not. Typical examples include a two-part permanent hair dye composed of a first part containing an alkali agent, an oxidation dye and optionally a direct dye such as a nitro dye and a second part containing an oxidizing agent; and a one-part semi-permanent hair dye containing an organic acid or an alkali agent, and an acid dye, basic dye or direct dye such as a nitro dye.

The above-described permanent hair dye is however accompanied by the drawback that the color tone imparted by an oxidation dye is not so vivid. Use of a nitro dye or cationic dye for a two-component hair dye containing an oxidizing agent has been attempted in order to produce various color tones (refer to, for example, Japanese Patent Laid-Open Nos. 271435/1994 and 2001-261535). A hair dye added with a nitro dye develops a vivid color just after dyeing, but color fades away remarkably over time and tends to be dull. Use of a cationic dye, on the other hand, involves such problems that it is easily decomposed when mixed with a peroxide serving as an oxidizing agent and it cannot readily be used in combination with an anionic polymer.

SUMMARY OF THE INVENTION

An object of the present invention is to provide a hair dye composition comprising a dissociative direct dye represented by the following formula (1):

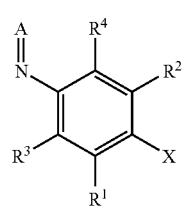

(1)

wherein, $R^1$, $R^2$, $R^3$ and $R^4$ each independently represents a hydrogen atom or a substituent, X represents a hydroxyl group or $-NHSO_2R^5$, in which $R^5$ represents an alkyl, aryl or heterocyclic group, and A represents a group represented by any one of the below-described formulas (Cp-1) through (Cp-12) with the proviso that the above-described groups may have one or more substituents:

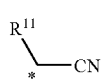

(Cp-1)

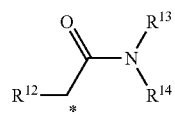

(Cp-2)

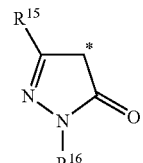

(Cp-3)

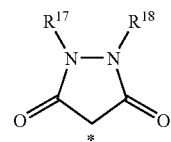

(Cp-4)

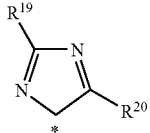

(Cp-5)

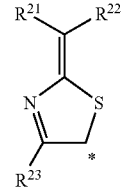

(Cp-6)

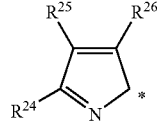

(Cp-7)

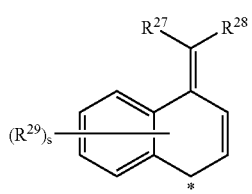

(Cp-8)

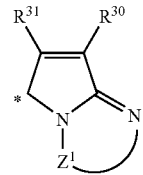

(Cp-9)

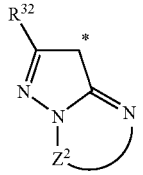

(Cp-10)

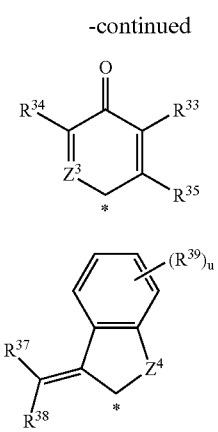

(in formulas (Cp-1) through (Cp-12), * is a position bonding to the nitrogen atom in formula (1), in formula (Cp-1), $R^{11}$ represents a cyano group, acyl group, aryl group, heterocyclic group or a group —$C(R^{101})$=$C(R^{102})$—$R^{103}$, in which $R^{101}$, $R^{102}$ and $R^{103}$ each independently represents a hydrogen atom or a substituent with the proviso that at least one of $R^{102}$ and $R^{103}$ is an electron attractive group having a Hammett σp value of 0.1 or greater, in formula (Cp-2), $R^{12}$ represents a cyano, alkoxycarbonyl, carbamoyl, aryl or heterocyclic group, and $R^{13}$ and $R^{14}$ each independently represents a hydrogen atom or an alkyl, aryl or heterocyclic group, in formula (Cp-3), $R^{15}$ represents a hydrogen atom or an alkyl, aryl, heterocyclic, amino, alkylamino, arylamino, heterocyclic amino, alkoxy, acylamino, alkoxycarbonylamino, ureido, alkoxycarbonyl, carbamoyl or cyano group, and $R^{16}$ represents a hydrogen atom or an alkyl, aryl or heterocyclic group, in formula (Cp-4), $R^{17}$ and $R^{18}$ each independently represents a hydrogen atom or an alkyl, aryl or heterocyclic group, in formula (Cp-5), $R^{19}$ and $R^{20}$ each independently represents a hydrogen atom or an alkyl, aryl or heterocyclic group, in formula (Cp-6), $R^{21}$ and $R^{22}$ each independently represents a cyano, carbamoyl, alkoxycarbonyl, alkylsulfonyl or arylsulfonyl group, and $R^{23}$ represents a hydrogen atom or an alkyl, aryl or heterocyclic group, in formula (Cp-7), $R^{24}$, $R^{25}$ and $R^{26}$ each independently represents a hydrogen atom or a substituent, in formula (Cp-8), $R^{27}$ and $R^{28}$ each independently represents a cyano, carbamoyl, alkoxycarbonyl, alkylsulfonyl or arylsulfonyl group, $R^{29}$ represents a substituent, and s stands for an integer of from 0 to 6, in formula (Cp-9), $R^{30}$ and $R^{31}$ each independently represents a hydrogen atom or a substituent, and $Z^1$ represents an atomic group necessary for the formation of a 6-membered ring together with N—C=N, in formula (Cp-10), $R^{32}$ represents a hydrogen atom or a substituent, and $Z^2$ represents an atomic group necessary for the formation of a 6-membered ring together with N—C=N, in formula (Cp-11), $R^{33}$, $R^{34}$ and $R^{35}$ each independently represents a hydrogen atom or a substituent, $Z^3$ represents a nitrogen atom or —$C(R^{36})$=, and $R^{36}$ represents a hydrogen atom or a substituent, with the proviso that when $Z^3$ represents —$C(R^{36})$=, $R^{34}$ and $R^{36}$ may be coupled to form a 5-membered or 6-membered ring, and in formula (Cp-12), $R^{37}$ and $R^{38}$ each independently represents a cyano, carbamoyl, alkoxycarbonyl, alkylsulfonyl or arylsulfonyl group, $R^{39}$ represents a hydrogen atom or a substituent, u stands for an integer of from 0 to 4 and $Z_4$ represents —$SO_2$— or —SO—), or salt thereof.

DETAILED DESCRIPTION OF THE INVENTION

The present invention relates to a hair dye composition capable of dyeing the hair strongly into a vivid color tone without causing decomposition of the dye during the dyeing process, and exhibiting an excellent resistance against sunlight, hair washing, perspiration, friction and heat, having a high stability against an alkali agent and an oxidizing agent, having high dyeing properties, and not fading away easily even after passage of time; and a hair dyeing method using the composition.

The dissociative direct dye of formula (1) used in the present invention has a phenolic hydroxyl group or a sulfonamide group —$NHSO_2R^5$. At a certain pH or greater, proton dissociation occurs in the dye, which causes a change in color hue, thereby imparting a desired color hue to the hair. The dissociative direct dye (1) preferably does not contain, in the molecule thereof, a group which dissociates at a neutral pH such as carboxyl group, sulfo group or quaternary ammonium group.

In formula (1), examples of the substituent represented by $R^1$, $R^2$, $R^3$, or $R^4$ include halogen atoms, alkyl groups, alkenyl groups, alkynyl groups, aryl groups, heterocyclic groups, a cyano group, a hydroxy group, a nitro group, a carboxyl group, alkoxy groups, aryloxy groups, silyloxy groups, heterocyclic oxy groups, acyloxy groups, carbamoyloxy groups, alkoxycarbonyloxy groups, aryloxycarbonyloxy groups, an amino group, alkylamino groups, arylamino groups, heterocyclic amino groups, acylamino groups, ureido groups, alkoxycarbonylamino groups, aryloxycarbonylamino groups, sulfamoylamino groups, alkylsulfonylamino groups, arylsulfonylamino groups, a mercapto group, alkylthio groups, arylthio groups, heterocyclic thio groups, sulfamoyl groups, a sulfo group, alkylsulfinyl groups, arylsulfinyl groups, alkylsulfonyl groups, arylsulfonyl groups, acyl groups, alkoxycarbonyl groups, aryloxycarbonyl groups, carbamoyl groups, arylazo groups, heterocyclic azo groups, phosphino groups, phosphinyl groups, phosphinyloxy groups, phosphinylamino groups and silyl groups. When these substituents are further substitutable, they may have one or more substituents.

Specific examples of the above-described substituents (including the case where they are substituted further) will next be described.

The halogen atoms include fluorine, chlorine, bromine and iodine atoms.

The alkyl groups include linear, branched or cyclic $C_{1-10}$, preferably $C_{1-6}$ alkyl groups such as methyl, ethyl, n-propyl, isopropyl, t-butyl, n-octyl, 2-chloroethyl, 2-cyanoethyl, 2-ethylhexyl, cyclopropyl and cyclopentyl.

The alkenyl groups include linear, branched or cyclic $C_{2-10}$, preferably $C_{2-6}$ alkenyl groups such as vinyl, allyl, prenyl and cyclopenten-1-yl.

The alkynyl groups include $C_{2-10}$, preferably $C_{2-6}$ alkynyl groups such as ethynyl and propargyl.

The aryl groups include $C_{6-12}$, preferably $C_{6-8}$ aryl groups such as phenyl, p-tolyl, naphthyl, 3-chlorophenyl and 2-aminophenyl.

The heterocyclic groups include aromatic or nonaromatic, monovalent $C_{1-12}$, preferably $C_{2-6}$ groups obtained by removing one hydrogen atom from 5- or 6-membered heterocyclic compounds, such as 1-pyrazolyl, 1-imidazolyl, 2-furyl, 2-thienyl, 2-thiazolyl, benzothiazol-2-yl, isothiazol-5-yl, benzoisothiazol-7-yl, oxazol-2-yl, benzoxazol-2-yl, 1,2,4-thiadiazol-5-yl, 1,3,4-thiadiazol-2-yl, 1,2,4-oxadiazol-5-yl, 1,3,4-oxadiazol-2-yl, 1,2,4-triazol-3-yl, 4-pyridyl, 3-pyridyl, 4-pyrimidinyl and qunazolin-4-yl.

The alkoxy groups include linear, branched or cyclic, $C_{1-10}$, preferably $C_{1-6}$ alkoxy groups such as methoxy, ethoxy, isopropoxy, t-butoxy, cyclopentyloxy, 2-buten-1-yloxy and 2-methoxyethoxy.

The aryloxy groups include $C_{6-12}$, preferably $C_{6-8}$ aryloxy groups such as phenoxy, 2-methylphenoxy, 4-t-butylphenoxy and 3-nitrophenoxy.

The silyloxy groups include $C_{3-10}$, preferably $C_{3-6}$ silyloxy groups such as trimethylsilyloxy and t-butyldimethylsilyloxy.

The heterocyclic oxy groups include $C_{1-12}$, preferably $C_{2-6}$ heterocyclic oxy groups such as 1-phenyltetrazol-5-oxy and 2-tetrahydropyranyloxy.

The acyloxy groups include $C_{1-12}$, preferably $C_{1-8}$ acyloxy groups such as formyloxy, acetyloxy, pivaloyloxy, benzoyloxy and p-methoxyphenylcarbonyloxy.

The carbamoyloxy groups include $C_{1-10}$, preferably $C_{1-6}$ carbamoyloxy groups such as N,N-dimethylcarbamoyloxy, N,N-diethylcarbamoyloxy, morpholinocarbonyloxy, and N-n-octylcarbamoyloxy.

The alkoxycarbonyloxy groups include $C_{2-10}$, preferably $C_{2-6}$ alkoxycarbonyloxy groups such as methoxycarbonyloxy, ethoxycarbonyloxy, t-butoxycarbonyloxy and n-octyloxycarbonyloxy.

The aryloxycarbonyloxy groups include $C_{7-12}$, preferably $C_{7-10}$ aryloxycarbonyloxy groups such as phenoxycarbonyloxy and p-methoxyphenoxycarbonyloxy.

The alkylamino groups include $C_{1-10}$, preferably $C_{1-6}$ alkylamino groups such as methylamino and dimethylamino.

The arylamino groups include $C_{6-12}$, preferably $C_{6-8}$ arylamino groups such as anilino, N-methylanilino and diphenylamino).

The heterocyclic amino groups include $C_{1-12}$, preferably $C_{2-6}$ heterocyclic amino groups such as imidazol-2-ylamino and pyrazol-3-ylamino.

The acylamino groups include $C_{1-10}$, preferably $C_{1-6}$ alkylcarbonylamino groups such as formylamino, acetylamino and pivaloylamino, $C_{6-12}$, preferably $C_{6-8}$ arylcarbonylamino groups such as benzoylamino, $C_{2-12}$, preferably $C_{2-6}$ heterocyclic carbonylamino groups such as pyridine-4-carbonylamino, thiophene-2-carbonylamino and morpholinocarbonylamino, and $C_{2-10}$, preferably $C_{4-8}$ imido groups such as N-succinimido and N-phthalimido.

The ureido groups include $C_{1-12}$, preferably $C_{1-6}$ ureido groups such as carbamoylamino, N,N-dimethylureido and N,N-diethylureido.

The alkoxycarbonylamino groups include $C_{2-10}$, preferably $C_{2-6}$ alkoxycarbonylamino groups such as methoxycarbonylamino, ethoxycarbonylamino and t-butoxycarbonylamino.

The aryloxycarbonylamino groups include $C_{7-12}$, preferably $C_{7-9}$ aryloxycarbonylamino groups such as phenoxycarbonylamino, p-chlorophenoxycarbonylamino and 4-methoxyphenoxycarbonylamino.

The sulfamoylamino groups include $C_{0-10}$, preferably $C_{0-6}$ sulfamoylamino groups such as sulfamoylamino, N,N-dimethylaminosulfonylamino and N-(2-hydroxyethyl)sulfamoylamino.

The alkylsulfonylamino groups include $C_{1-10}$, preferably $C_{1-6}$ alkylsulfonylamino groups such as methylsulfonylamino and butylsulfonylamino.

The arylsulfonylamino groups include $C_{6-12}$, preferably $C_{6-8}$ arylsulfonylamino groups such as phenylsulfonylamino, 2,3,5-trichlorophenylsulfonylamino and p-methylphenylsulfonylamino.

The alkylthio groups include $C_{1-10}$, preferably $C_{1-6}$ alkylthio groups such as methylthio, ethylthio and butylthio.

The arylthio groups include $C_{6-12}$, preferably $C_{6-8}$ arylthio groups such as phenylthio, p-chlorophenylthio and m-methoxyphenylthio.

The heterocyclic thio groups include $C_{2-10}$, preferably $C_{2-6}$ heterocyclic thio groups such as 2-benzothiazolylthio and 1-phenyltetrazol-5-ylthio.

The sulfamoyl groups include $C_{0-10}$, preferably $C_{0-6}$ sulfamoyl groups such as sulfamoyl, N-ethylsulfamoyl, N,N-dimethylsulfamoyl, N-acetylsulfamoyl and N-benzoylsulfamoyl.

The alkylsulfinyl groups include $C_{1-10}$, preferably $C_{1-6}$ alkylsulfinyl groups such as methylsulfinyl and ethylsulfinyl.

The arylsulfinyl groups include $C_{6-12}$, preferably $C_{6-8}$ arylsulfinyl groups such as phenylsulfinyl and p-methylphenylsulfinyl.

The alkylsulfonyl groups include $C_{1-10}$, preferably $C_{1-6}$ alkylsulfonyl groups such as methylsulfonyl and ethylsulfonyl.

The arylsulfonyl groups include $C_{6-12}$, preferably $C_{6-8}$ arylsulfonyl groups such as phenylsulfonyl and p-chlorophenylsulfonyl.

The acyl groups include formyl group, $C_{2-10}$, preferably $C_{2-6}$ alkylcarbonyl groups such as acetyl, pivaloyl and 2-chloroacetyl, and $C_{7-12}$, preferably $C_{7-9}$ arylcarbonyl groups such as benzoyl and 2,4-dichlorobenzoyl.

The alkoxycarbonyl groups include $C_{2-10}$, preferably $C_{2-6}$ alkoxycarbonyl groups such as methoxycarbonyl, ethoxycarbonyl, t-butoxycarbonyl and isobutoxycarbonyl.

The aryloxycarbonyl groups include $C_{7-12}$, preferably $C_{7-9}$ aryloxycarbonyl groups such as phenoxycarbonyl, 2-chlorophenoxycarbonyl, 3-nitrophenoxycarbonyl and 4-t-butylphenoxycarbonyl.

The carbamoyl groups include $C_{1-10}$, preferably $C_{1-6}$ carbamoyl groups such as carbamoyl, N-methylcarbamoyl, N,N-dimethylcarbamoyl, N-(2-hydroxyethyl)carbamoyl and N-(methylsulfonyl)carbamoyl.

The arylazo groups include $C_{6-12}$, preferably $C_{6-8}$ arylazo groups such as phenylazo and p-chlorophenylazo.

The heterocyclic azo groups include $C_{1-10}$, preferably $C_{1-6}$ heterocyclic azo groups such as pyrazol-3-ylazo, thiazol-2-ylazo, 5-ethylthio-1,3,4-thiadiazol-2-ylazo.

The phosphino groups include $C_{2-12}$, preferably $C_{2-6}$ phosphino groups such as dimethylphosphino, diphenylphosphino and methylphenoxyphosphino.

The phosphinyl groups include $C_{2-12}$, preferably $C_{2-6}$ phosphinyl groups such as phosphinyl and diethoxyphosphinyl.

The phosphinyloxy groups include $C_{2-12}$, preferably $C_{2-6}$ phosphinyloxy groups such as diphenoxyphosphinyloxy and dibutoxyphosphinyloxy.

The phosphinylamino groups include $C_{2-12}$, preferably $C_{2-6}$ phosphinylamino groups such as dimethoxyphosphinylamino and dimethylaminophosphinylamino.

The silyl groups include $C_{3-12}$, preferably $C_{3-8}$ Silyl groups such as trimethylsilyl, t-butyldimethylsilyl and phenyldimethylsilyl.

When the above-described substituents $R^1$, $R^2$, $R^3$ and $R^4$ are further substitutable, they may have one or more substituents. In such a case, preferable substituents are the same substituent groups as described above and a preferable range of the total number of the carbon atoms of $R^1$, $R^2$, $R^3$ and $R^4$ does not exceed the above-described range. When they have two or more substituents, the substituents may be the same or different.

In $-NHSO_2R^5$ represented by X in formula (1), the preferable number of carbon atoms of the alkyl group, aryl group or heterocyclic group represented by $R^5$ and specific examples of the group are the same as those described above in the substituents represented by $R^1$ to $R^4$.

In the group represented by A, that is, a group represented by any one of formulas (Cp-1) through (Cp-12) in formula (1), the preferable number of carbon atoms of the group represented by $R^{11}$ to $R^{39}$ and $R^{101}$ to $R^{103}$ and specific examples of the group are the same as those described above in the substituents represented by $R^1$ to $R^4$, with the proviso that at least one of $R^{102}$ and $R^{103}$ is an electron attractive group having a Hammett $\sigma_p$ value of 0.1 or greater, preferably 0.2 or greater. Examples of the electron attractive group having a Hammett $\sigma_p$ value of 0.1 or greater include a chlorine, bromine or iodine atom, or an alkoxycarbonyl, carbamoyl, alkylaminocarbonyl, dialkylaminocarbonyl, sulfamoyl, alkylaminosulfonyl, dialkylaminosulfonyl or acyl group. The Hammett empirical rule was advocated by L. P. Hammett in 1935 in order to quantitatively discuss the influence of a substituent on the reaction or equilibrium of a benzene derivative and its validity is now recognized widely. The substituent constants determined by the Hammett rule are $\sigma_p$ and $\sigma_m$ values. These values are found generally in many books and described in detail, for example, in *Lange's Handbook of Chemistry*, 12 ed., 1979, ed. J. A. Dean, (published by McGraw-Hill), *Journal of Japanese Chemistry*, Extra Number, 122, 96–103 (1979) (published by Nankodo) and *Chemical Review*, 91, 165–195 (1991).

The preferable range of dissociative direct dye (1) will next be described.

As $R^1$ or $R^2$ in formula (1), preferred are a hydrogen atom, halogen atoms, alkyl groups, a cyano group, acylamino groups, ureido groups, alkoxycarbonylamino groups, aryloxycarbonylamino groups, sulfamoylamino groups, alkylsulfonylamino groups, arylsulfonylamino groups, alkoxycarbonyl groups, sulfamoyl groups and carbamoyl groups, of which a hydrogen atom, a chlorine atom, a bromine atom, alkyl groups, a cyano group, acylamino groups, ureido groups, alkoxycarbonylamino groups, alkylsulfonylamino groups, arylsulfonylamino groups and carbamoyl groups are more preferred, with hydrogen and chlorine atoms and acylamino and carbamoyl groups being most preferred.

As $R^3$ or $R^4$ in formula (1), preferred are a hydrogen atom, halogen atoms, alkyl groups and acylamino groups, of which a hydrogen atom, chlorine atom and alkyl groups are more preferred, with a hydrogen atom being most preferred.

As X in formula (1), a hydroxyl group is more preferred. When X represents $-NHSO_2R^5$, $R^5$ preferably represents an alkyl group.

As A in formula (1), the below-described groups are preferred.

In formula (Cp-1), preferred as $R^{11}$ are a cyano group, acyl groups, heterocyclic groups and $-C(R^{101})=C(R^{102})-R^{103}$, with the following groups being particularly preferred.

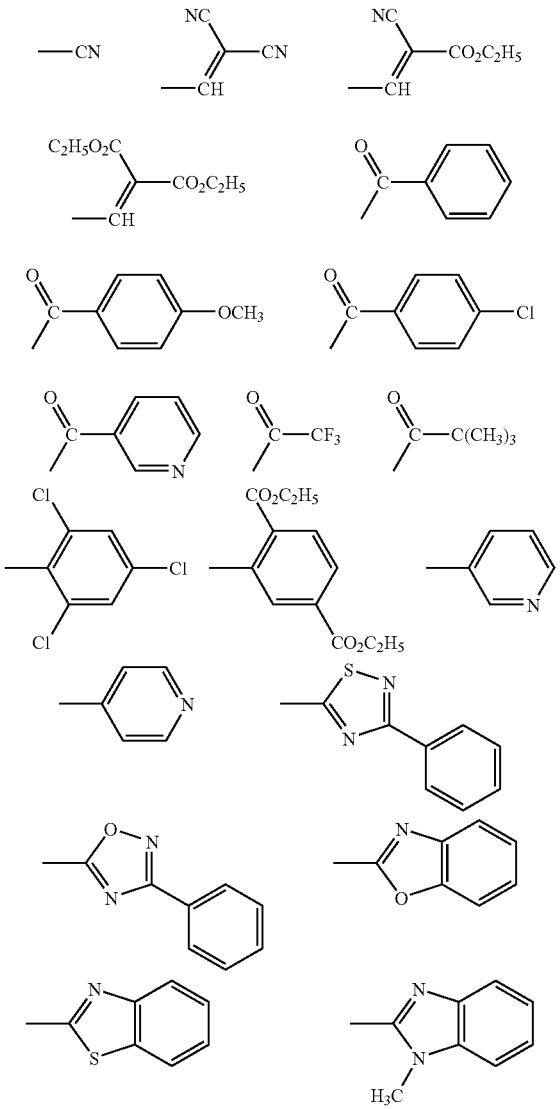

In formula (Cp-2), preferred as $R^{12}$ are a cyano group, aryl groups and heterocyclic groups. The cyano group and heterocyclic groups exemplified above as particularly preferred specific examples as $R^{11}$ are also preferred as $R^{12}$. As $R^{13}$ and $R^{14}$, a hydrogen atom, alkyl groups and aryl groups are preferred. It is preferred that at least one of $R^{13}$ and $R^{14}$ represents a hydrogen atom.

In formula (Cp-3), preferred as $R^{15}$ are alkyl groups, amino group, alkylamino groups, arylamino groups, heterocyclic amino groups, alkoxy groups, acylamino groups, alkoxycarbonylamino groups, ureido group, alkoxycarbonyl groups, carbamoyl groups and a cyano group, of which alkyl groups, acylamino groups, alkoxycarbonyl groups and a cyano group are more preferred. As $R^{16}$, aryl groups and heterocyclic groups are preferred, with aryl groups being most preferred.

In formula (Cp-4), preferred as $R^{17}$ and $R^{18}$ are alkyl groups and aryl groups.

In formula (Cp-5), preferred as $R^{19}$ and $R^{20}$ are aryl groups and heterocyclic groups, with aryl groups being most preferred.

In formula (Cp-6), preferred as $R^{21}$ and $R^{22}$ are a cyano group, carbamoyl groups and alkoxycarbonyl groups, of which a cyano group and alkoxycarbonyl groups are more preferred. As $R^{23}$, a hydrogen atom and alkyl groups are preferred.

In formula (Cp-7), preferred as $R^{24}$ are hydrogen atom, aryl groups, acylamino groups, alkylsulfonylamino groups and arylsulfonylamino groups. As $R^{25}$ and $R^{26}$, a hydrogen atom, aryl groups, alkoxycarbonyl groups, carbamoyl groups, alkylsulfonyl groups, arylsulfonyl groups and a cyano group are preferred, with aryl groups, alkoxycarbonyl groups, carbamoyl groups and a cyano group being more preferred.

In formula (Cp-8), preferred as $R^{27}$ and $R^{28}$ are a cyano group, carbamoyl groups and alkoxycarbonyl groups, while as $R^{29}$, halogen atoms, acylamino groups, alkylsulfonylamino groups, arylsulfonylamino groups, alkoxycarbonyl groups, carbamoyl groups, alkylsulfonyl groups and arylsulfonyl groups are preferred. As s, an integer of from 0 to 2 is preferred.

In formula (Cp-9), preferred as $R^{30}$ and $R^{31}$ are a hydrogen atom, alkyl groups, aryl groups, heterocyclic groups, alkoxycarbonyl groups, carbamoyl groups, alkylsulfonyl groups, arylsulfonyl groups and a cyano group, of which alkyl groups, aryl groups, alkoxycarbonyl groups, carbamoyl groups and a cyano group are more preferred. As $Z^1$, groups capable of forming the below-described ring systems are preferred.

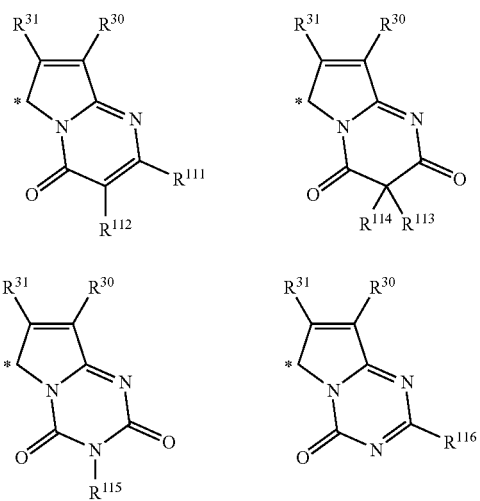

wherein, $R^{111}$ represents a hydrogen atom or an alkoxy, amino, alkylamino, arylamino, heterocyclic amino, acylamino, ureido, alkoxycarbonylamino, aryloxycarbonylamino, sulfamoylamino, alkylsulfonylamino, arylsulfonylamino, alkylthio, arylthio or heterocyclic thio group, $R^{112}$ represents a hydrogen or halogen atom, or an alkyl, acyl, carbamoyl or alkoxycarbonyl group, $R^{113}$ and $R^{114}$ each independently represents a hydrogen atom or an alkyl group, $R^{115}$ represents a hydrogen atom or an alkyl group, and $R^{116}$ represents a hydrogen atom or an alkyl, aryl, alkoxy, aryloxy, amino, alkylamino, arylamino, heterocyclic amino, acylamino, ureido, alkoxycarbonylamino, alkylsulfonylamino, arylsulfonylamino, alkylthio or arylthio group.

The preferable number of the carbon atoms of $R^{111}$ to $R^{116}$ and specific examples thereof are similar to those described above for the substituents represented by $R^1$ to $R^4$.

In formula (Cp-10), preferred as $R^{32}$ are hydrogen atom, alkyl groups, aryl groups, heterocyclic groups, alkoxycarbonyl groups, carbamoyl groups, alkylsulfonyl groups, arylsulfonyl groups and a cyano group, of which alkyl groups, aryl groups, alkoxycarbonyl groups, carbamoyl groups and a cyano group are more preferred. As $Z^2$, groups capable of forming the below-described ring systems are preferred.

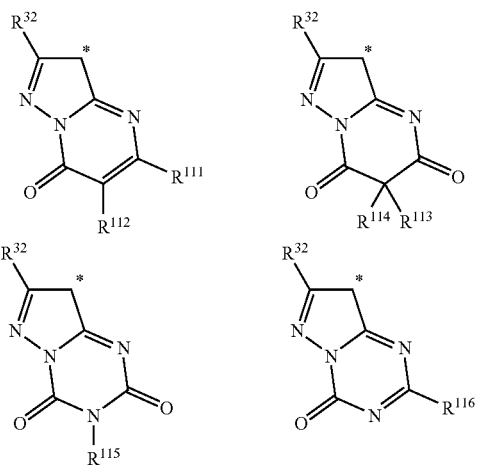

wherein, $R^{111}$ to $R^{116}$ have the same meanings as described above.

In formula (Cp-11), $Z^3$ preferably represents —C($R^{36}$)=, and preferred are the case where $R^{36}$ is a hydrogen atom or an acylamino group, $R^{33}$ and $R^{34}$ each represents a hydrogen atom, a halogen atom, an alkyl group or acylamino group, and $R^{35}$ represents a hydrogen atom or an alkyl group, and the case where $R^{34}$ and $R^{36}$ are coupled together to form a benzene ring which may be substituted with a halogen atom or an amino, alkylamino, arylamino, heterocyclic amino, acylamino, ureido, alkoxycarbonylamino, alkylsulfonylamino or arylsulfonylamino group, $R^{33}$ represents an acylamino, alkylsulfonylamino, arylsulfonylamino, carbamoylamino or sulfamoyl group, and $R^{35}$ represents a hydrogen atom.

In formula (Cp-12), preferred as $R^{37}$ and $R^{38}$ are a cyano group and alkoxycarbonyl groups, preferred as $R^{39}$ are halogen atoms, acylamino groups, alkylsulfonylamino groups, arylsulfonylamino groups, alkoxycarbonyl groups, carbamoyl groups, alkylsulfonyl groups and arylsulfonyl groups, preferred as u is an integer of from 0 to 2, and preferred as $Z^4$ is —SO$_2$—.

Among the dissociative direct dyes (1), those having as A the group of formula (Cp-1), (Cp-2), (Cp-3), (Cp-4), (Cp-7), (Cp-9) or (Cp-11) are more preferred, of which those having as A the group of formula (Cp-1), (Cp-2), (Cp-3) or (Cp-11) are particularly preferred.

Preferable specific examples of the dissociative direct dye (1) will be shown below.
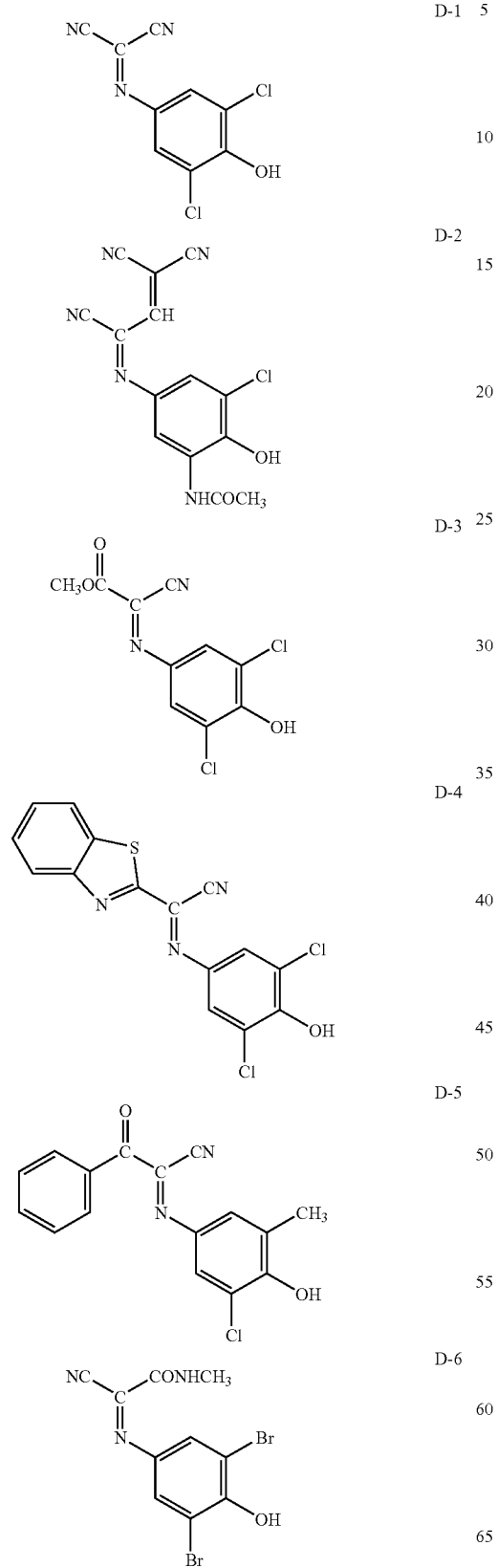
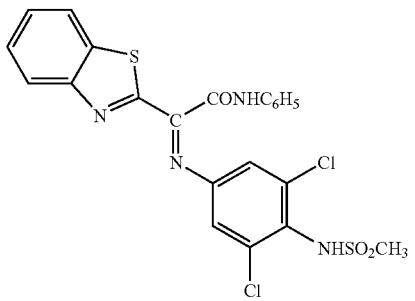
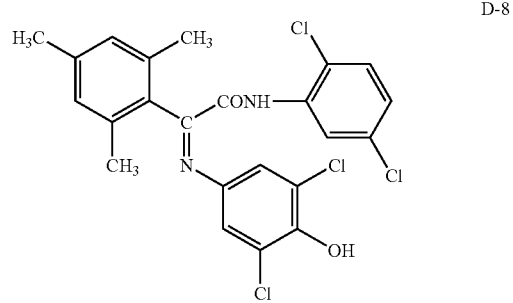
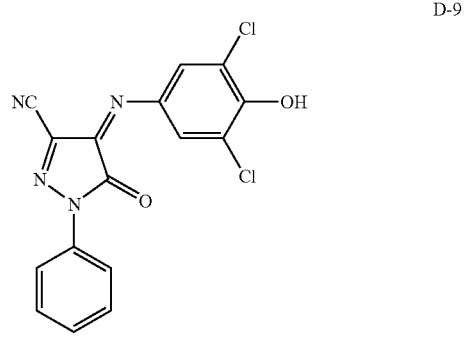
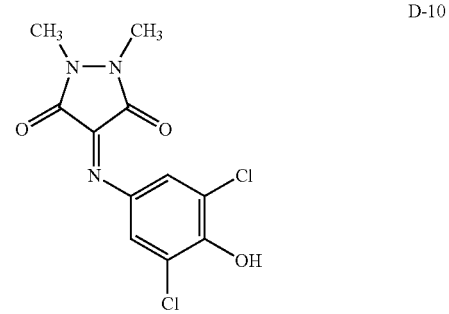
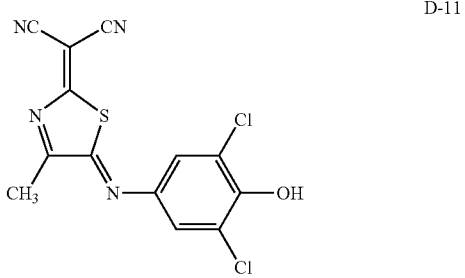

-continued
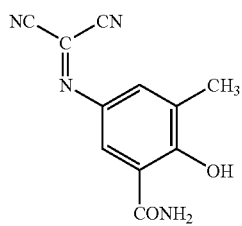
D-12
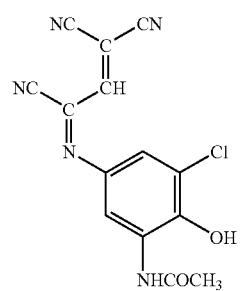
D-13
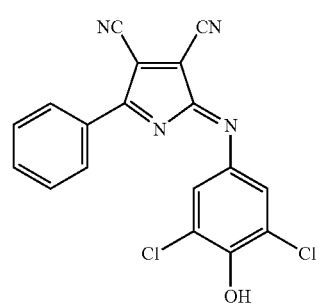
D-14
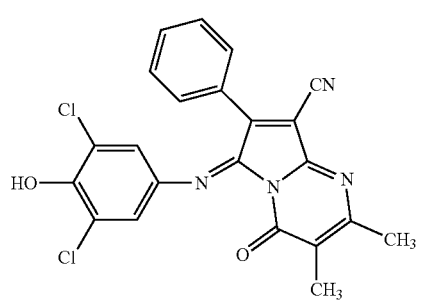
D-15
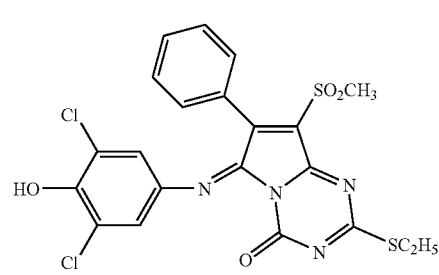
D-16
-continued
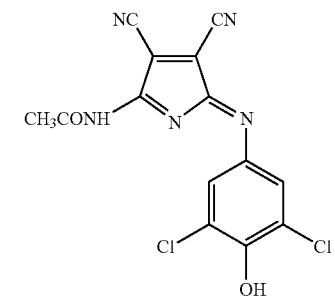
D-17
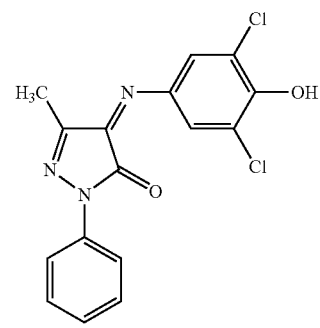
D-18
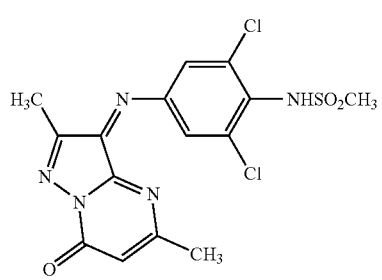
D-19
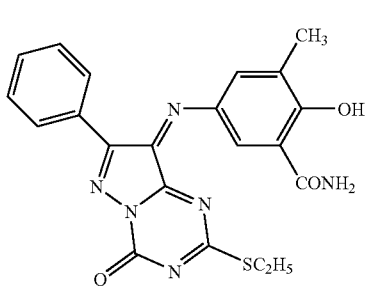
D-20
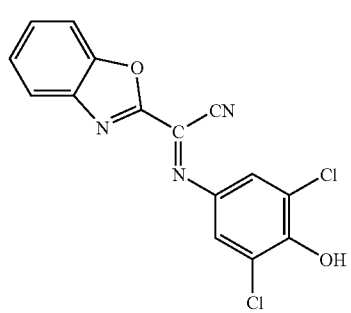
D-21

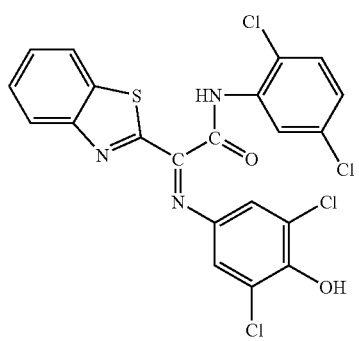
D-22
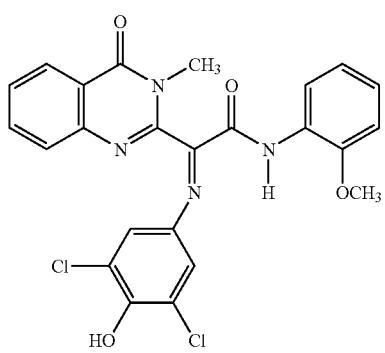
D-23
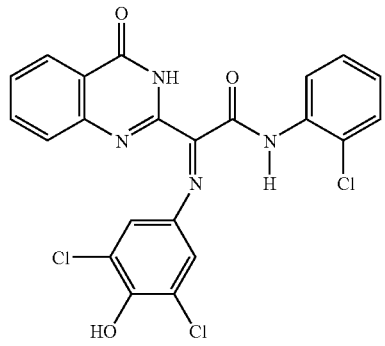
D-24
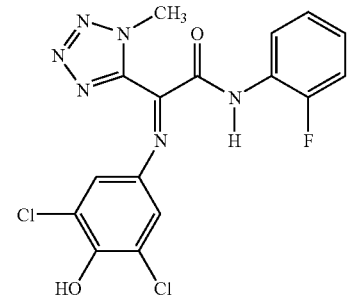
D-25
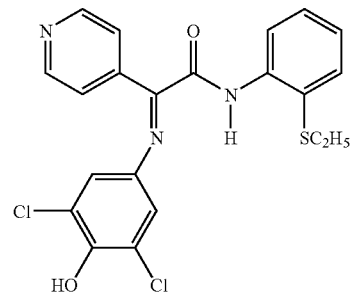
D-26
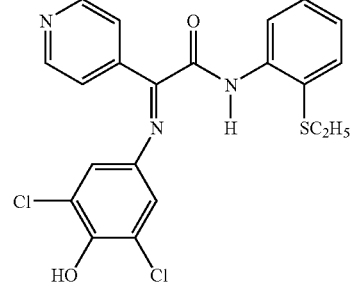
D-27
D-28
D-29
D-30
D-31

-continued
D-32
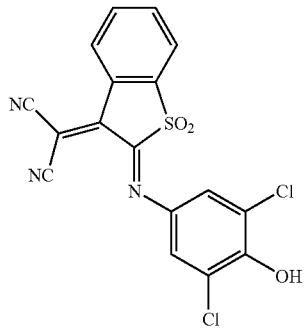
D-33
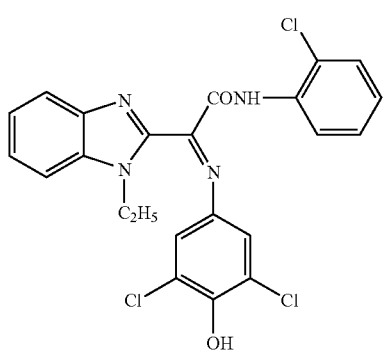
D-34
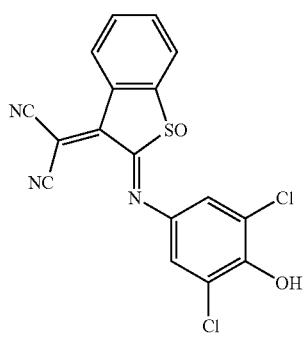
D-35
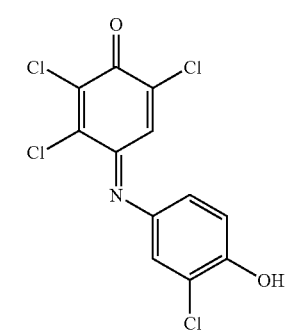
-continued
D-36
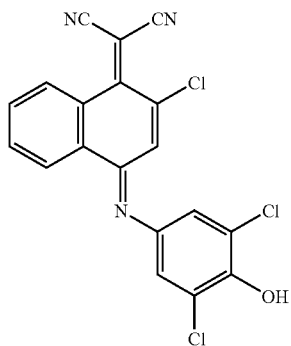
D-37
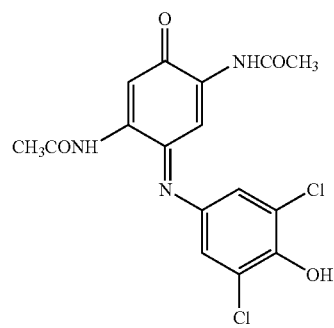
D-38
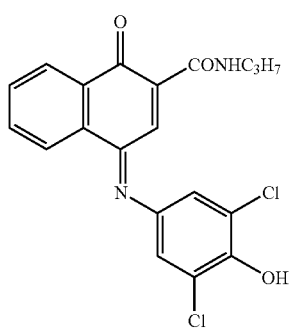
D-39
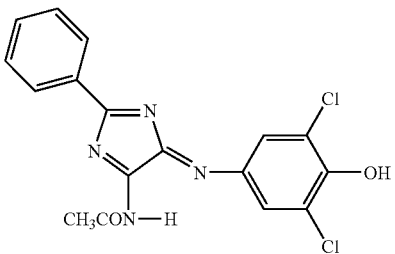
D-40
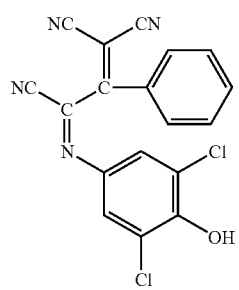

-continued
D-41
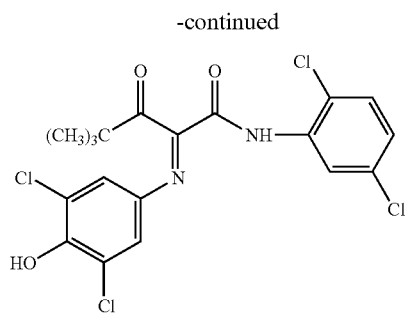
D-42
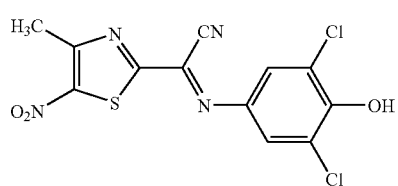
D-43
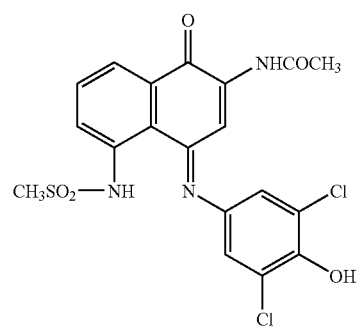
D-44
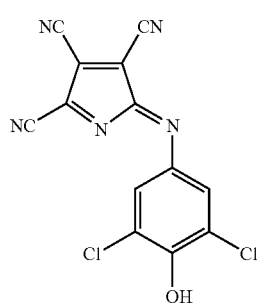
D-45
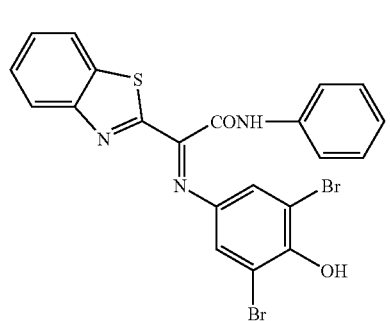
-continued
D-46
D-47
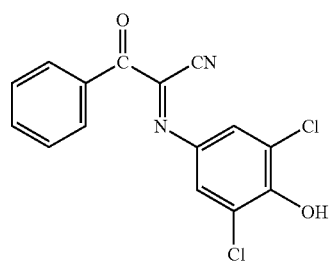
D-48
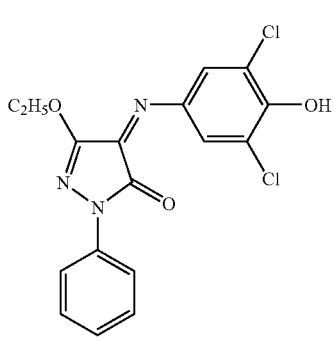
D-52
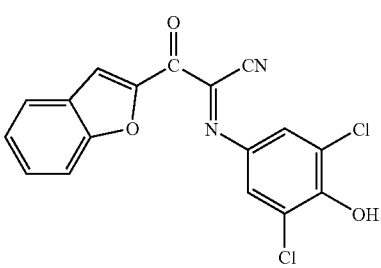
D-49
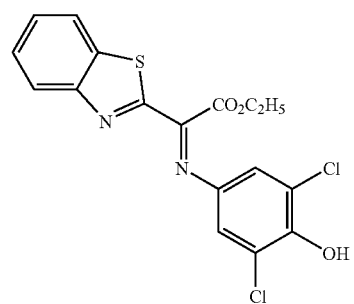

D-50

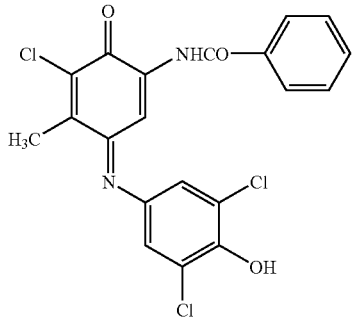

D-51

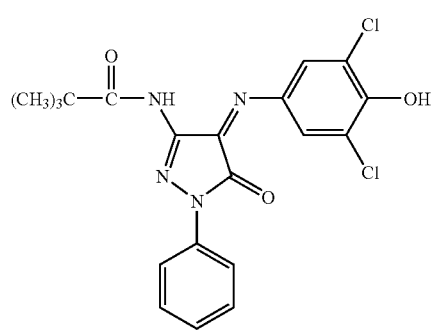

The dissociative direct dye (1) may be a salt of an organic or inorganic acid, or a salt of an organic or inorganic alkali. Examples of the organic or inorganic acid include hydrochloric acid, sulfuric acid, phosphoric acid, acetic acid, propionic acid, lactic acid and citric acid, while those of the organic or inorganic alkali include ammonium hydroxide, 2-ethanolamnonium hydroxide, sodium hydroxide and potassium hydroxide.

The dissociative direct dye (1) can be synthesized in accordance with the below-described reaction scheme. Specifically, Dye-1, which is a dissociative direct dye (1), is available by condensing Int-1 (wherein, Y represents a hydrogen atom, a halogen atom or a group capable of being dissociated as an anion) which is a coupler compound and Int-2, which is a p-aminophenol (or p-sulfonamidoaniline) derivative, in the presence of a base and an oxidizing agent. In the below-described scheme, V—C—W corresponds to A in formula (1).

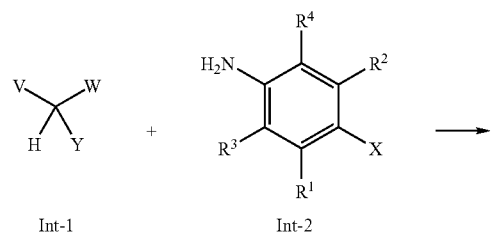

Int-1    Int-2

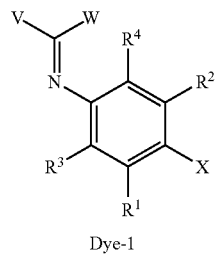

Dye-1

A coupler compound such as Int-1 can be synthesized in accordance with a process as described in the literature on a coupler in the field of silver halide color photosensitive materials. Specifically, the process as described in the literature cited on pp. 613 to 617 of Research Disclosure 40145 (September, 1997), or the process as described on pp. 80 to 83 of Research Disclosure 37038 (February, 1995) can be adopted.

The pKa of the dissociative direct dye (1) is preferably from 1.5 to 9, especially preferably from 2 to 8, most preferably from 2 to 7.5, from the viewpoint of hair coloring performance and color retention attained by the dye. The pKa value can be determined in the following manner. First, a sample is dissolved in a 1:1 (volume ratio) solution of DMF and water to give its final concentration of $2 \times 10^{-5}$ mol/L. After adjustment of the pH of the resulting solution to 2 with 1.0 mol/L hydrochloric acid, the solution was titrated with a 1.0 mol/L aqueous solution of sodium hydroxide. Variations in a visible ultraviolet absorption spectrum is recorded and an inflection point is determined by regression analysis.

In the hair dye composition of the present invention, the dissociative direct dye (1) can be used in combination with another direct dye or an oxidation dye.

Examples of such a direct dye include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 46 (C.I. 110825), Basic Red 76 (C.I. 12245), Basic Red 118 (C.I. 12251:1), Basic Yellow 28 (C.I. 48054) and Basic Yellow 57 (C.I. 12719); cationic dyes as described in Japanese Patent Laid-Open Nos. 2204/1983 and 118832/1997, and Japanese Language Laid-Open Publications (PCT) Nos. 501322/1996 and 507545/1996; and methine type cationic dyes having a cyanine structure represented by the following formulas:

yellow dye

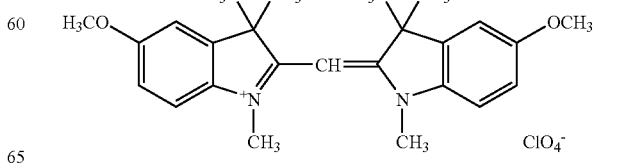

-continued

Orange dye

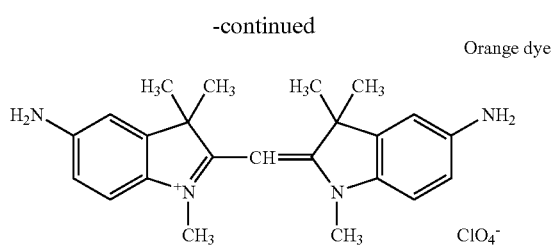

The dissociative direct dye (1) is added preferably in an amount of 0.0001 to 20 wt. %, more preferably 0.001 to 20 wt. %, more preferably from 0.05 to 10 wt. %, especially preferably from 0.1 to 5 wt. % based on the whole composition (after mixing of all the component parts when the composition is a two part or three part composition; this will be applied equally hereinafter). When another direct dye is used in combination, the total content of the dissociative direct dye (1) and the another direct dye preferably ranges from 0.001 to 20 wt. %, more preferably from 0.01 to 20 wt. %, still more preferably from 0.05 to 10 wt. %, especially preferably from 0.1 to 5 wt. %.

In the hair dye composition of the present invention, the dissociative direct dye (1) exhibits a high storage stability within a wide pH range from 2 to 11 which is a pH range employed ordinarily for hair dyes, so that the hair dye composition of the present invention can be used at any pH in the above-described pH range. Use in a pH range of from 5 or greater is however preferred from the viewpoint of dyeing property. Moreover, owing to the high stability of the dissociative direct dye (1) against an alkali agent, the hair dye composition of the present invention can be used at a pH 8 or greater, particularly 8 to 11 which permits the composition to exhibit a high dyeing property, so that even after long storage, a high dyeing property can be kept without causing decomposition of the direct dye.

Examples of the alkali agent used for the hair dye composition of the present invention include ammonia, alkanolamines such as monoethanolamine and isopropanolamine or salts thereof, guanidium salts such as guanidine carbonate, and hydroxides such as sodium hydroxide. The alkali agent is added preferably in an amount of from 0.01 to 20 wt. %, more preferably 0.1 to 10 wt. %, especially preferably 0.5 to 5 wt. % based on the whole composition.

Since the dissociative direct dye (1) has a high stability against an oxidizing agent, it can be applied to the hair after mixing with an oxidizing agent. In other words, it can be provided as a two-part composition composed of a first part containing the dissociative direct dye (1) and a second part containing an oxidizing agent. In this case, hair dyeing and bleaching can be carried out simultaneously, which facilitates more vivid hair dyeing.

Examples of the oxidizing agent include hydrogen peroxide, persulfates such as ammonium persulfate, potassium persulfate and sodium persulfate, perborates such as sodium perborate, percarbonates such as sodium percarbonate and bromates such as sodium bromate and potassium bromate. Hydrogen peroxide is especially preferred from the viewpoints of hair bleaching property, stability and effectiveness of the dissociative direct dye (1). Hydrogen peroxide may be used in combination with another oxidizing agent. The oxidizing agent is added preferably in an amount of from 0.5 to 10 wt. %, especially preferably from 1 to 8 wt. %, based on the whole composition.

The first part containing the dissociative direct dye (1) and the second part containing the oxidizing agent are mixed at a volume ratio preferably ranging from 2:1 to 1:3.

In the hair dye composition of the present invention, an oxidation dye can be used in combination with the dissociative direct dye (1). Such combined use enables considerably vivid and intense dyeing which cannot be accomplished by the single use of the oxidation dye. For the oxidation dye, known developers and couplers ordinarily employed for an oxidation type hair dye can be used.

Examples of the developer include paraphenylenediamine, toluene-2,5-diamine, 2-chloro-paraphenylenediamine, N-methoxyethyl-paraphenylenediamine, N,N-bis(2-hydroxyethyl)-paraphenylenediamine, 2-(2-hydroxyethyl)-paraphenylenediamine, 2,6-dimethyl-paraphenylenediamine, 4,4'-diaminodiphenylamine, 1,3-bis(N-(2-hydroxyethyl)-N-(4-aminophenyl)amino)-2-propanol, PEG-3,2,2'-paraphenylenediamine, paraaminophenol, paramethylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraaminopyrimidine, 2,5,6-triamino-4-hydroxypyrimidine and 4,5-diamino-1-(4'-chlorobenzyl)pyrazole and salts thereof.

Examples of the coupler include metaphenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, metaaminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-metaaminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, and 2,6-diaminopyridine and salts thereof.

As each of the developer and coupler, at least two of the above-described developer or coupler are usable. The content of each of them is preferably from 0.01 to 20 wt. %, especially preferably from 0.5 to 10 wt. % based on the whole composition.

To the hair dye composition of the present invention, an autoxidation dye typified by an indole or an indoline, or a known direct dye such as a nitro dye or a disperse dye can also be added.

Addition of a polyol, polyol alkyl ether, cationic or amphoteric polymer or silicone to the hair dye composition of the present invention is preferred, because the resulting composition can dye the hair uniformly and has improved cosmetic effects of the hair.

In addition to the above-described components, those ordinarily employed as a raw material for cosmetics can be added to the hair dye composition of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, anionic surfactants, protein derivatives, amino acids, antiseptics, chelating agents, stabilizers, antioxidants, plant extracts, crude drug extracts, vitamins, colorants, perfumes and ultraviolet absorbers.

The hair dye composition of the present invention can be prepared in a conventional manner to form a one-part composition, a two-part composition having a first part containing an alkali agent and a second part containing an oxidizing agent, or a three-part composition having, in addition to these two parts, a powdery oxidizing agent such as persulfate. The direct dye (1) may be incorporated in at least one of these parts of the two-part or three-part composition. The direct dye (1) may be incorporated in at least one of these parts of the two-part or three-part composition. When the hair dye composition of the present invention is one-part type, it is applied to the hair directly, while when it is two- or three-part type, these parts are mixed upon hair dyeing and the mixture is applied to the hair.

In the case of preparation of the hair dye composition of the present invention as a two-part type, the first part is typically prepared by mixing the dissociative direct dye (1) and optionally an oxidation dye and adjusting the pH of the mixture to 8 to 12 with an alkali agent such as ammonia. The second part is prepared by incorporating about 2 to 6 wt. % of hydrogen peroxide, adjusting the mixture to weakly acidic with phosphoric acid. When the composition is a three-part type, a persulfate is mixed with an inert substance such as talc or dextrin and a bonding agent to convert the mixture into a granular substance containing about 5 to 95 wt. % of persulfate. The granular substance is added to a mixture of the first part and the second part upon use.

The hair dye composition of the present invention can be provided in the form of powder, transparent liquid, emulsion, cream, gel, paste, aerosol, aerosol foam or the like. It preferably has a viscosity of 2000 to 100000 mPa·s upon its application to the hair (after mixing of all the parts when the composition is a two-part or three-part type). The above-described viscosity is measured at 20° C. by using a Brookfield rotary viscometer (No. 5 spindle, 5 rpm).

EXAMPLES

The synthesis examples of the dissociative direct dye (1) will next be described specifically.

Synthesis Example 1

Synthesis of Exemplified Compound D-50

Synthesis was conducted in accordance with the following scheme.

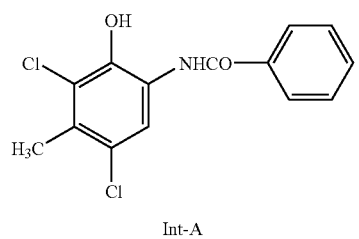

Int-A

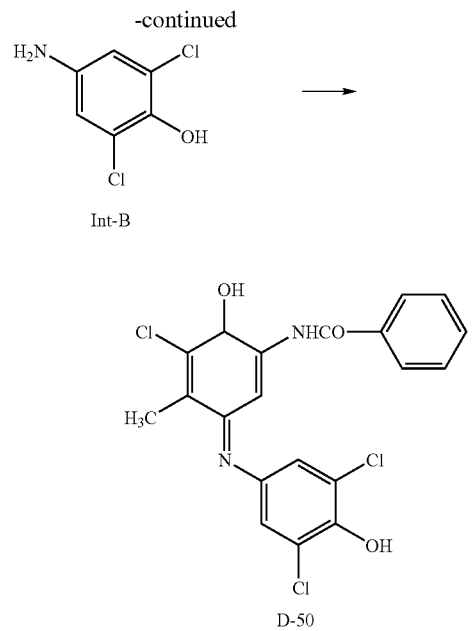

To 100 mL of ethyl acetate were added 2.96 g of N-(3, 5-dichloro-2-hydroxy-4-methylphenyl)benzamide (Int-A), 2.10 g of commercially available 4-amino-2,6-dichlorophenol (Int-B), and 5.6 mL of triethylamine. The resulting mixture was stirred at room temperature. After addition of 3.5 g of silver acetate in several portions, stirring of the mixture was continued for 3 hours. The reaction mixture was filtered under reduced pressure. The cake on the Nutsche was added to 200 mL of acetone. The mixture was heated under reflux for 1 hour under stirring, followed by hot filtration. To the filtrate was added 1 mL of concentrated hydrochloric acid and the mixture was concentrated under reduced pressure. To the residue were added acetonitrile and water to disperse the former in the latter. The crystals thus precipitated were collected by filtration. After washing while pouring water, the crystals thus obtained were air dried, whereby 2.47 g of Exemplified Compound D-50 was obtained as dark purple crystals (yield: 57%).

Synthesis Example 2

Synthesis of Exemplified Compound D-38

Synthesis was conducted in accordance with the following scheme.

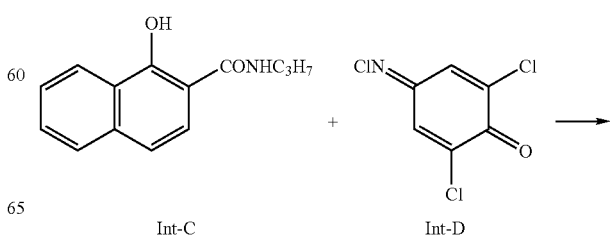

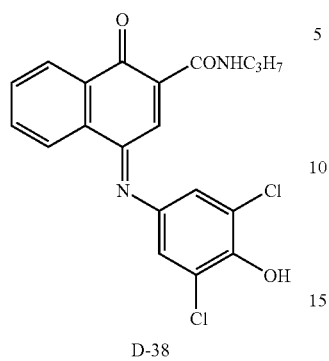

D-38

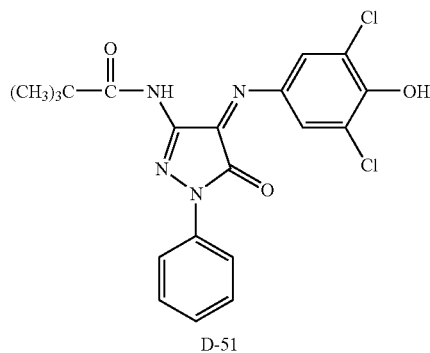

D-51

To 50 mL of ethyl acetate were added 2.37 g of N-propyl-1-hydroxy-2-naphthamide (Int-C) and 2.8 mL of triethylamine. The resulting mixture was stirred at room temperature. After addition of 2.20 g of commercially available 2,6-dichloroquinone-4-chloroimide (Int-D) in several portions, stirring was continued for 2 hours. To the reaction mixture were added 30 mL of acetonitrile and dilute hydrochloric acid (obtained by diluting 1.9 mL of concentrated hydrochloric acid with 10 mL of water). The resulting mixture was stirred for 30 minutes. The crystals thus precipitated were filtered under reduced pressure and then washed while pouring thereon 50 mL of water and then 20 mL of acetonitrile. The crystals were air dried, whereby 2.5 g of Exemplified D-38 was obtained as dark red crystals (yield: 62%).

Synthesis Example 3

Synthesis of Exemplified Compound D-51

Synthesis was conducted in accordance with the following scheme:

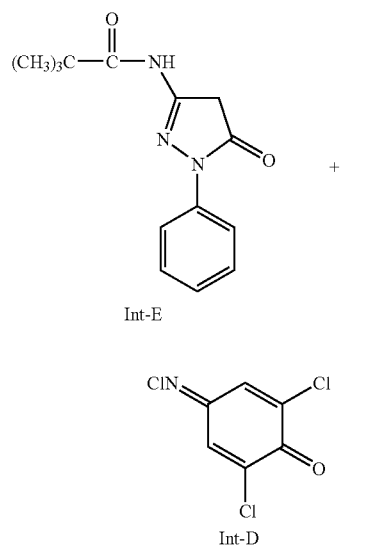

To 50 mL of ethyl acetate were added 2.59 g of N-(1-phenyl-5-pyrazolon-3-yl)pivaloylamide (Int-E) and 2.8 mL of triethylamine. The resulting mixture was stirred at room temperature. After addition of 2.20 g of commercially available 2,6-dichloroquinone-4-chloroimide (Int-D) in several portions, stirring was continued for 2 hours. The reaction mixture was washed with dilute hydrochloric acid. The organic layer was washed with water twice, dried over anhydrous magnesium sulfate and concentrated under reduced pressure. The residue was purified by chromatography on a silica gel column (eluent: 2:1 mixed solvent of chloroform and ethyl acetate). The eluate was concentrated under reduced pressure. Acetonitrile (10 mL) was added to the residue to crystallize the same. The crystals thus precipitated were collected by filtration, washed while pouring a small amount of acetonitrile thereon, and air dried, whereby 0.44 g of Exemplified Compound D-51 was obtained as crystals (yield: 10%).

Synthesis 4

Synthesis of Exemplified Compound D-4

Synthesis was conducted in accordance with the following scheme.

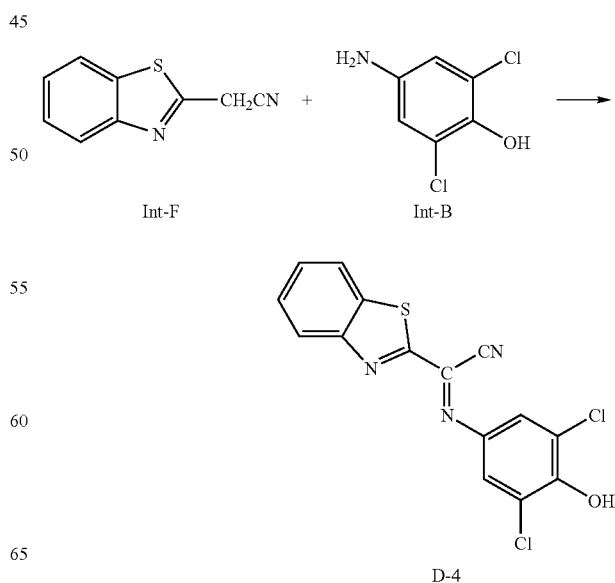

Benzothiazol-2-yl-acetonitrile (Int-F, 3.48 g), 3.92 g of commercially available 4-amino-2,6-dichlorophenol (Int-B), 16.6 g of anhydrous potassium carbonate, 60 mL of ethyl acetate, 40 mL of water and 20 mL of ethanol were mixed. The resulting mixture was stirred at room temperature. To the reaction mixture was added 11.0 g of ammonium persulfate in 6 portions over 30 minutes and stirring was continued for 2 hours. The reaction mixture was filtered under reduced pressure. The cake on the Nutsche was added to 120 mL of water and the mixture was stirred at room temperature. Concentrated hydrochloric acid was added slowly to make the reaction mixture acidic (about pH 3 when measured by pH test paper). The crystals were collected by filtration and washed while pouring thereon 60 mL of water and then air dried, whereby 5.24 g of Exemplified Compound D-4 was obtained as yellowish brown crystals (yield: 75%).

Examples 1 to 4

Hair dye foams as shown in Table 1 were prepared in a manner known per se in the art.

TABLE 1

| Component (wt. %) | Examples | | | |
|---|---|---|---|---|
| | 1 | 2 | 3 | 4 |
| Dye (D-50) | 0.5 | — | — | — |
| Dye (D-38) | — | 0.5 | — | — |
| Dye (D-51) | — | — | 0.5 | — |
| Dye (D-4) | — | — | — | 0.5 |
| Monoethanolamine | 1 | 1 | 1 | 1 |
| Ethanol | 15 | 15 | 15 | 15 |
| Propylene glycol | 10 | 10 | 10 | 10 |
| Polyoxyethylene (20) octyldodecyl ether | 10 | 10 | 10 | 10 |
| Polyoxyethylene (9) tridecyl ether | 3 | 3 | 3 | 3 |
| Polyoxyethylene (3) tridecyl ether | 6 | 6 | 6 | 6 |
| Oleic diethanolamide | 8 | 8 | 8 | 8 |
| Oleyl alcohol | 2 | 2 | 2 | 2 |
| Ammonium chloride | q.s. *1 | q.s. *1 | q.s. *1 | q.s. *1 |
| LPG (4.0 kg/cm$^2$) | 10 | 11 | 12 | 12 |
| Purified water | Balance | Balance | Balance | Balance |

*1: an amount to adjust the pH to 8.5

The above-described hair dye foams were each applied to the goat hair at 30° C. and was caused to act on the hair for 20 minutes. The hair thus dyed was then washed with an ordinarily used shampoo, followed by drying. As a result of the observation of the color tone of the dyed hair, it exhibited good dyeing property and resistance to shampoo.

Examples 5 to 9

Two-part hair dyes as shown in Table 2 were prepared in a manner known per se in the art.

TABLE 2

| Component (wt. %) | Examples | | | | |
|---|---|---|---|---|---|
| | 5 | 6 | 7 | 8 | 9 |
| 1-st part | | | | | |
| Dye (D-50) | 0.5 | — | — | 0.5 | — |
| Dye (D-38) | — | — | 0.5 | — | — |
| Dye (D-51) | — | — | — | — | 0.5 |
| Dye (D-4) | — | 0.5 | — | — | — |
| HC Red 3 | — | — | 0.2 | — | — |
| p-Aminophenol | — | — | — | 0.2 | 0.2 |
| p-Amino-o-cresol | — | — | — | 0.2 | 0.2 |
| Ammonia (28 wt. %) | 6 | 6 | 6 | 6 | 6 |
| Ethanol | 15 | 15 | — | — | — |
| Propylene glycol | 10 | 10 | 2 | 2 | 2 |
| Polyoxyethylene (20) octyldodecyl ether | 10 | 10 | — | — | — |
| Polyoxyethylene (40) cetyl ether | — | — | 2 | 2 | 2 |
| Polyoxyethylene (2) cetyl ether | — | — | 2.5 | 2.5 | 2.5 |
| Oleic diethanolamide | 8 | 8 | — | — | — |
| Oleyl alcohol | 2 | 2 | — | — | — |
| Stearyl-trimethylammonium chloride | — | — | 1.5 | 1.5 | 1.5 |
| Cetanol | — | — | 1 | 1 | 1 |
| Liquid paraffin | — | — | 0.5 | 0.5 | 0.5 |
| Ammonium chloride | q.s *2 | q.s *2 | q.s *2 | q.s *2 | q.s *2 |
| Sodium sulfite | — | — | — | 0.5 | 0.5 |
| Tetrasodium edetate | 0.1 | 0.1 | 0.1 | 0.1 | 0.1 |
| Purified water | Balance | Balance | Balance | Balance | Balance |
| 2-nd part | | | | | |
| Hydrogen peroxide | 6 | 6 | 6 | 6 | 6 |
| Methyl paraben | 0.1 | 0.1 | 0.1 | 0.1 | 0.1 |
| Phosphoric acid | q.s. *3 | q.s. *3 | q.s. *3 | q.s. *3 | q.s. *3 |
| Purified water | Balance | Balance | Balance | Balance | Balance |

*2: an amount to adjust the pH to 9.8.
*3: an amount to adjust the pH to 3.5

After 1 part by weight of the first part was mixed with 1 part by weight of the second part, the resulting mixture was applied to the goat hair at 30° C. and was caused to act on the hair for 20 minutes. The hair thus dyed was then washed with an ordinarily used shampoo, followed by drying. As a result of the observation of the color tone of the dyed hair, it exhibited good dyeing property and resistance to shampoo.

What is claimed is:

1. A hair dye composition comprising a dissociative direct dye represented by the following formula (1) or a salt thereof:

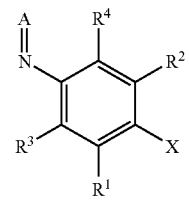

(1)

wherein, $R^1$, $R^2$, $R^3$ and $R^4$ each independently represents a hydrogen atom or a substituent, X represents a hydroxyl group or —NHSO$_2$R$^5$, in which R$^5$ represents an alkyl, aryl or heterocyclic group, A represents a group represented by any one of the below-described formulae which group may have one or more substituents:

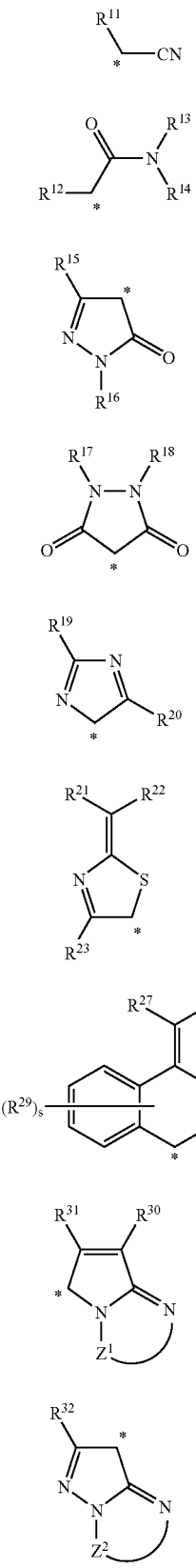

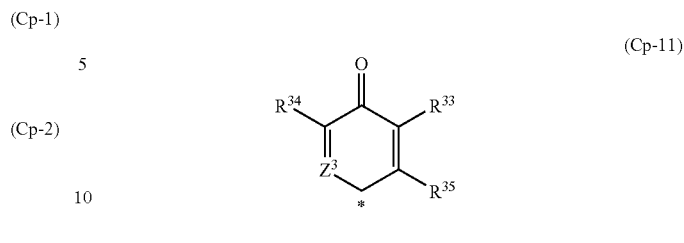

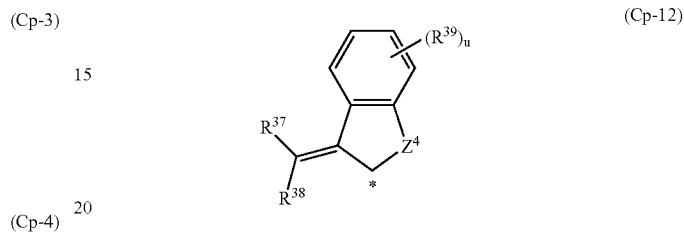

wherein * is a position bonding to the nitrogen atom in formula (1), in formula (Cp-1), $R^{11}$ represents a cyano, acyl, aryl or heterocyclic group, or $-C(R^{101})=C(R^{102})-R^{103}$, in which $R^{101}$, $R^{102}$ and $R^{103}$ each independently represents a hydrogen atom or a substituent with the proviso that at least one of $R^{102}$ and $R^{103}$ is an electron attractive group having a Hammett σp value of 0.1 or greater, in formula (Cp-2), $R^{12}$ represents a cyano, alkoxycarbonyl, carbamoyl, aryl or heterocyclic group, and $R^{13}$ and $R^{14}$ each independently represents a hydrogen atom or an alkyl, aryl or heterocyclic group, in formula (Cp-3), $R^{15}$ represents a hydrogen atom or an alkyl, aryl, heterocyclic, amino, alkylamino, arylamino, heterocyclic amino, alkoxy, acylamino, alkoxycarbonylamino, ureido, alkoxycarbonyl, carbamoyl or cyano group, and $R^{16}$ represents a hydrogen atom or an alkyl, aryl or heterocyclic group, in formula (Cp-4), $R^{17}$ and $R^{18}$ each independently represents a hydrogen atom or an alkyl, aryl or heterocyclic group, in formula (Cp-5), $R^{19}$ and $R^{20}$ each independently represents a hydrogen atom or an alkyl, aryl or heterocyclic group, in formula (Cp-6), $R^{21}$ and $R^{22}$ each independently represents a cyano, carbamoyl, alkoxycarbonyl, alkylsulfonyl or arylsulfonyl group, and $R^{23}$ represents a hydrogen atom or an alkyl, aryl or heterocyclic group, in formula (Cp-8), $R^{27}$ and $R^{28}$ each independently represents a cyano, carbamoyl, alkoxycarbonyl, alkylsulfonyl or arylsulfonyl group, $R^{29}$ represents a substituent, and s stands for an integer of from 0 to 6, in formula (Cp-9), $R^{30}$ and $R^{31}$ each independently represents a hydrogen atom or a substituent, and $Z^1$ represents an atomic group necessary for the formation of a 6-membered ring together with N—C=N, resulting in a ring system selected from the group consisting of:

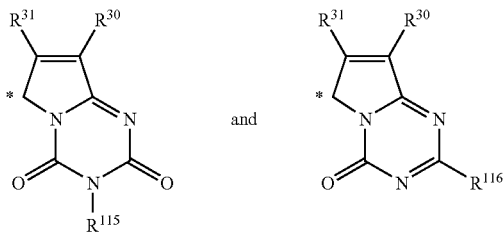

wherein $R^{115}$ represents a hydrogen atom or an alkyl group, and $R^{116}$ represents a hydrogen atom or an alkyl, aryl, alkoxy, aryloxy, amino, alkylamino, arylamino, heterocyclic amino, acylamino, ureido, alkoxycarbonylamino, alkylsulfonylamino, arylsulfonylamino, alkylthio, or arylthio group, in formula (Cp-10), $R^{32}$ represents a hydrogen atom or a substituent, and $Z^2$ represents an atomic group necessary for the formation of a 6-membered ring together with N—C=N, in formula (Cp-11), $R^{33}$, $R^{34}$ and $R^{35}$ each independently represents a hydrogen atom or a substituent, $Z^3$ represents a nitrogen atom or —C($R^{36}$)=, in which $R^{36}$ represents a hydrogen atom or a substituent, with the proviso that when $Z^3$ represents —C($R^{36}$)=, $R^{34}$ and $R^{36}$ may be coupled to form a 5-membered or 6-membered ring, and in formula (Cp-12), $R^{37}$ and $R^{38}$ each independently represents a cyano, carbamoyl, alkoxycarbonyl, alkylsulfonyl or arylsulfonyl group, $R^{39}$ represents a hydrogen atom or a substituent, u stands for an integer of from 0 to 4 and $Z^4$ represents —SO$_2$— or —SO.

2. The hair dye composition of claim 1, wherein $R^1$ and $R^2$ of the dissociative direct dye (1) are each a hydrogen or halogen atom, or an alkyl, cyano, acylamino, ureido, alkoxycarbonylamino, aryloxycarbonylamino, sulfamoylamino, alkylsulfonylamino, arylsulfonylamino, alkoxycarbonyl, sulfamoyl or carbamoyl group which may be substituted.

3. The hair dye composition of claim 1, wherein $R^3$ and $R^4$ of the dissociative direct dye (1) are each a hydrogen atom, a halogen atom, or an alkyl or acylamino group which may be substituted.

4. The hair dye composition of claim 1, wherein X of the dissociative direct dye (1) is a hydroxyl group or —NHSO$_2R^5$, and $R^5$ is an alkyl group which may be substituted.

5. The hair dye composition of claim 1, wherein A of the dissociative direct dye (1) is a group, which may have one or more substituents, selected from the group consisting of:

formula (Cp-1) in which $R^{11}$ is a cyano group, acyl group, heterocyclic group or group —C($R^{101}$)=C($R^{102}$)—$R^{103}$, formula (Cp-2) in which $R^{12}$ is a cyano group, aryl group or heterocyclic group and $R^{13}$ and $R^{14}$ are each a hydrogen atom, alkyl group or aryl group, with the proviso that at least one of $R^{13}$ and $R^{14}$ represents a hydrogen atom, formula (Cp-3) in which $R^{15}$ is an alkyl, amino, alkylamino, arylamino, heterocyclic amino, alkoxy, acylamino, alkoxycarbonylamino, ureido, alkoxycarbonyl, carbamoyl or cyano group, and $R^{16}$ is an aryl or heterocyclic group, formula (Cp-4) in which $R^{17}$ and $R^{18}$ are each an alkyl or aryl group, formula (Cp-5) in which $R^{19}$ and $R^{20}$ are each an aryl or heterocyclic group, formula (Cp-6) in which $R^{21}$ and $R^{22}$ are each a cyano, carbamoyl or alkoxycarbonyl and $R^{23}$ is a hydrogen atom or an alkyl group, formula (Cp-8) in which $R^{27}$ and $R^{28}$ are each a cyano, carbamoyl or alkoxycarbonyl group, $R^{29}$ is a halogen atom or an acylamino, alkylsulfonylamino, arylsulfonylamino, alkoxycarbonyl, carbamoyl, alkylsulfonyl or arylsulfonyl group, and s is an integer of from 0 to 2, formula (Cp-9) in which $R^{30}$ and $R^{31}$ are each a hydrogen atom or an alkyl, aryl, heterocyclic, alkoxycarbonyl, carbamoyl, alkylsulfonyl, arylsulfonyl or cyano group and $Z^1$ represents an atomic group necessary for the formation of a 6-membered ring together with N—C=N, resulting in a ring system selected from the group consisting of:

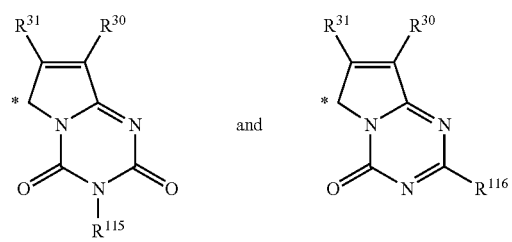

in which, $R^{115}$ represents a hydrogen atom or an alkyl group, and $R^{116}$ represents a hydrogen atom or an alkyl, aryl, alkoxy, aryloxy, amino, alkylamino, arylamino, heterocyclic amino, acylamino, ureido, alkoxycarbonylamino, alkylsulfonylamino, arylsulfonylamino, alkylthio, or arylthio group, formula (Cp-10) in which $R^{32}$ is a hydrogen atom or an alkyl, aryl, heterocyclic, alkoxycarbonyl, carbamoyl, alkylsulfonyl, arylsulfonyl or cyano group, and $Z^2$ is a group capable of forming the following ring systems:

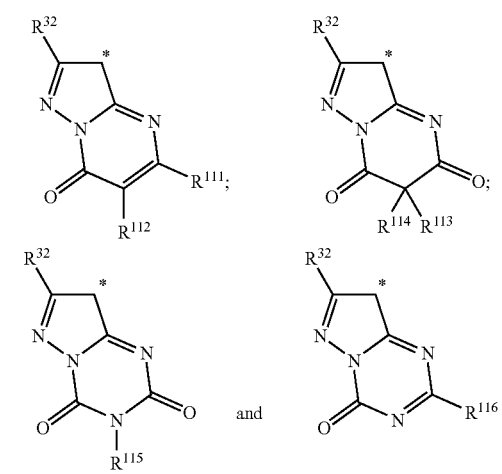

in which, $R^{111}$ represents a hydrogen atom or an alkoxy, amino, alkylamino, arylamino, heterocyclic amino, acylamino, ureido, alkoxycarbonylamino, aryloxycarbonylamino, sulfamoylamino, alkylsulfonylamino, arylsulfonylamino, alkylthio, arylthio or heterocyclic thio group, $R^{112}$ represents a hydrogen or halogen atom, or an alkyl, acyl, carbamoyl or alkoxycarbonyl group, $R^{113}$ and $R^{114}$ each independently represents a hydrogen atom or an alkyl group, $R^{115}$ represents a hydrogen atom or an alkyl group, and $R^{116}$ represents a hydrogen atom or an alkyl, aryl, alkoxy, aryloxy, amino, alkylamino, arylamino, heterocyclic amino, acylamino, ureido, alkoxycarbonylamino, alkylsulfonylamino, arylsulfonylamino, alkylthio, or arylthio group, formula (Cp-11) in which $Z^3$ is —C($R^{36}$)=, $R^{36}$ representing a hydrogen atom or an acylamino group, $R^{33}$ and $R^{34}$ are each a hydrogen atom, a halogen atom, an alkyl group or acylamino group, and $R^{35}$ is a hydrogen atom or an alkyl group; or in which $Z^3$ is —C($R^{36}$)=, $R^{34}$ and $R^{36}$ are coupled together to form a benzene ring which may be substituted with a halogen atom or an amino, alkylamino, arylamino, heterocyclic amino, acylamino, ureido, alkoxycarbonylamino, alkylsulfonylamino or arylsulfonylamino group, $R^{33}$ represents an acylamino, alkylsulfonylamino, arylsulfonylamino, carbamoyl or sulfamoyl group, and $R^{35}$ represents a hydrogen atom, and formula (Cp-12) in which $R^{37}$ and $R^{38}$ are a cyano or alkoxycarbonyl group, $R^{39}$ is a halogen atom or an acylamino, alkylsulfonylamino, arylsulfonylamino, alkoxycarbonyl, carbamoyl, alkylsulfonyl or arylsulfonyl group, u is an integer of from 0 to 2, and $Z^4$ is —SO$_2$—.

6. The hair dye composition of claim 1, wherein A of the dissociative direct dye (1) is a group represented by formula selected from the group consisting of (Cp-1), (Cp-2), (Cp-3), (Cp-4), (Cp-9), and (Cp-11).

7. The hair dye composition of claim 1, wherein A of the dissociative direct dye (1) is a group represented by formula (Cp-1), $R^{11}$ represents a cyano, acyl, aryl or heterocyclic group, or —C($R^{101}$)=C($R^{102}$)—$R^{103}$, in which $R^{101}$, $R^{102}$ and $R^{103}$ each independently represents a hydrogen atom or a substituent with the proviso that at least one of $R^{102}$ and $R^{103}$ is an electron attractive group having a Hammett σp value of 0.1 or greater.

8. The hair dye composition of claim 1, wherein A of the dissociative direct dye (1) is a group represented by formula (Cp-2), $R^{12}$ represents a cyano, alkoxycarbonyl, carbamoyl, aryl or heterocyclic group, and $R^{13}$ and $R^{14}$ each independently represents a hydrogen atom or an alkyl, aryl or heterocyclic group.

9. The hair dye composition of claim 1, wherein A of the dissociative direct dye (1) is a group represented by formula (Cp-3), $R^{15}$ represents a hydrogen atom or an alkyl, aryl, heterocyclic, amino, alkylamino, arylamino, heterocyclic amino, alkoxy, acylamino, alkoxycarbonylamino, ureido, alkoxycarbonyl, carbamoyl or cyano group, and $R^{16}$ represents a hydrogen atom or an alkyl, aryl or heterocyclic group.

10. The hair dye composition of claim 1, wherein A of the dissociative direct dye (1) is a group represented by formula (Cp-11), $R^{33}$, $R^{34}$ and $R^{35}$ each independently represents a hydrogen atom or a substituent, $Z^3$ represents a nitrogen atom or —C($R^{36}$)=, in which $R^{36}$ represents a hydrogen atom or a substituent, with the proviso that when $Z^3$ represents —C($R^{36}$)=, $R^{34}$ and $R^{36}$ may be coupled to form a 5-membered or 6-membered ring.

11. The hair dye composition of claim 1, wherein said direct dye represented by formula (1) is selected from the group consisting of:

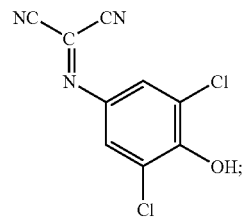
D-1

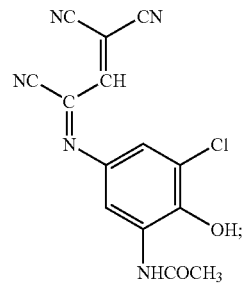
D-2

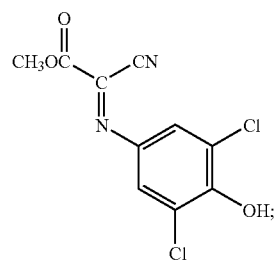
D-3

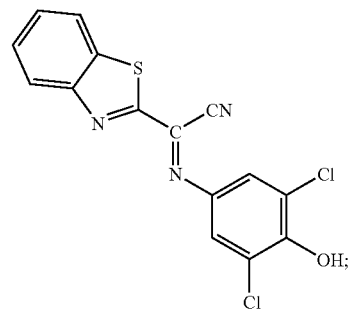
D-4

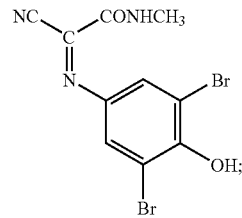
D-6

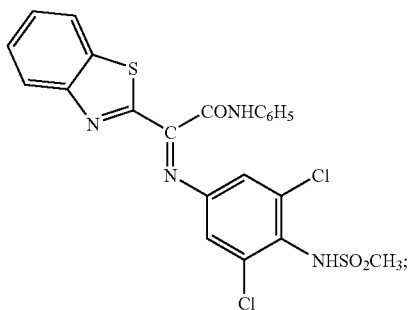
D-7

-continued
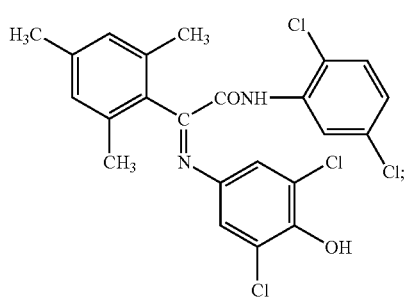 D-8
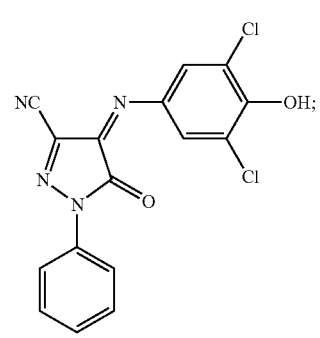 D-9
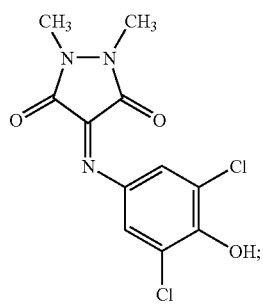 D-10
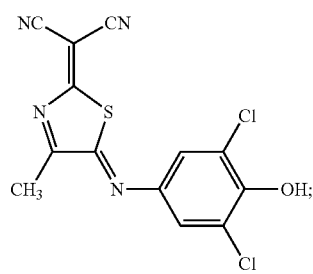 D-11
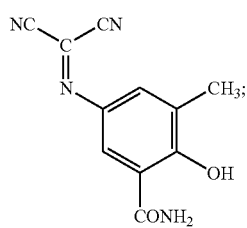 D-12
-continued
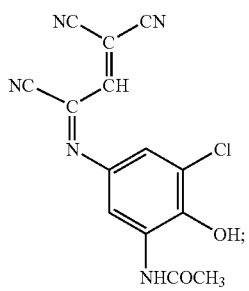 D-13
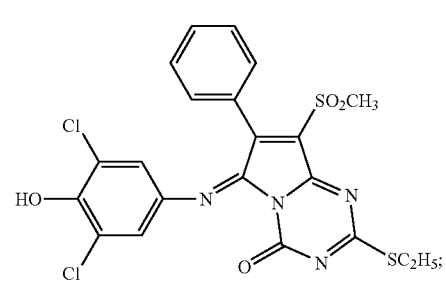 D-16
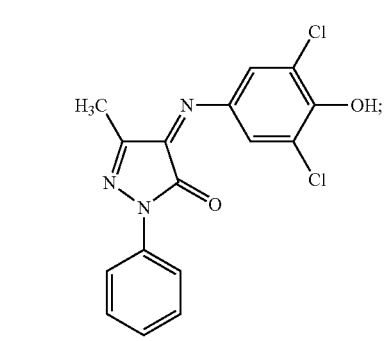 D-18
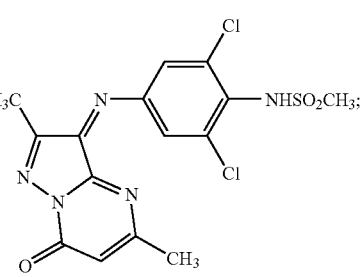 D-19
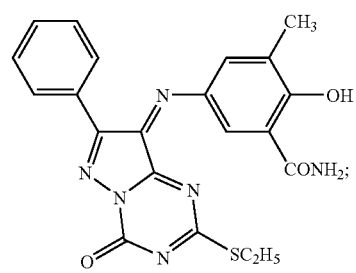 D-20

-continued
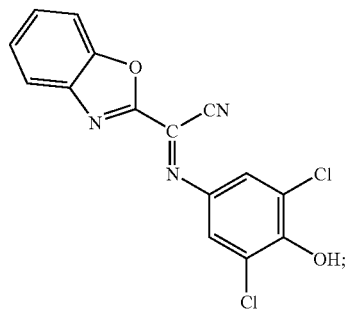
D-21
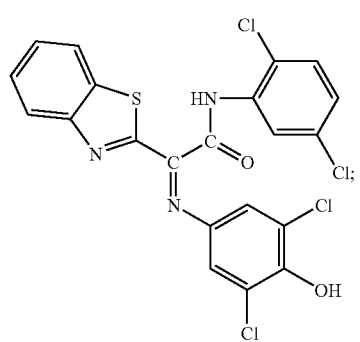
D-22
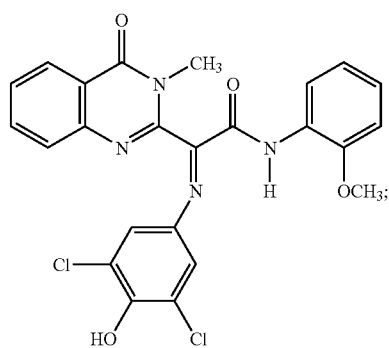
D-23
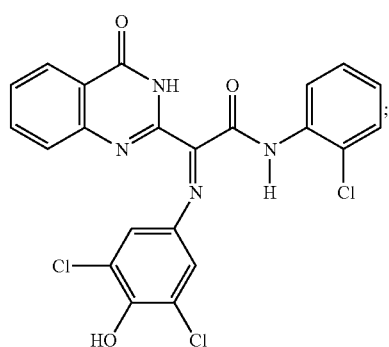
D-24
-continued
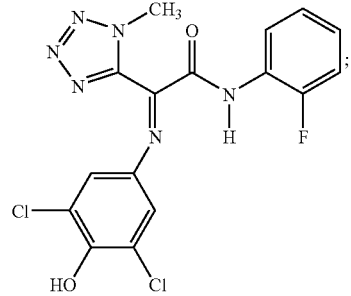
D-25
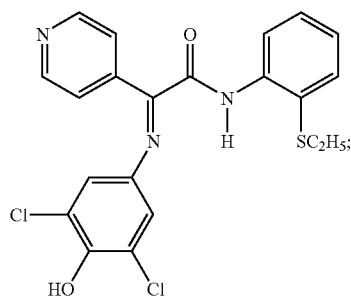
D-26
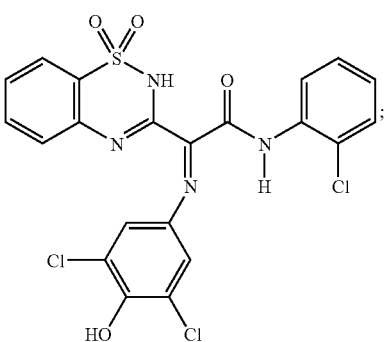
D-27
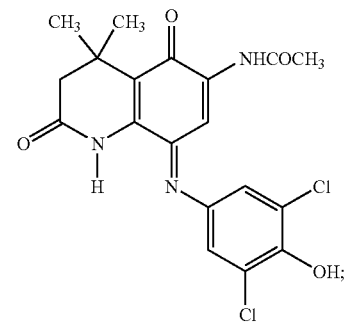
D-28
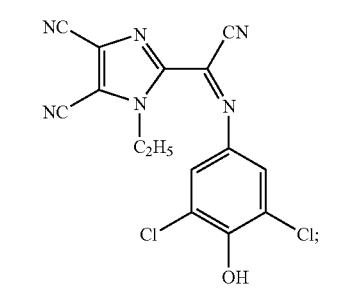
D-29

-continued
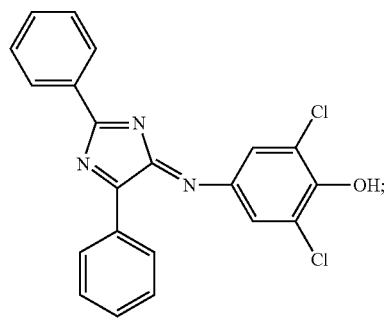
D-30
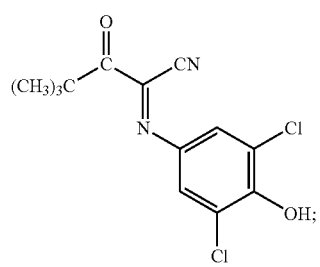
D-31
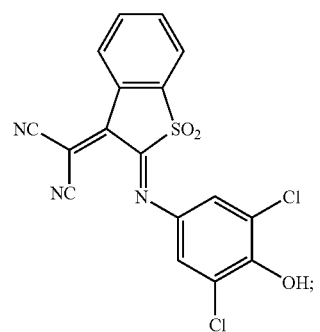
D-32
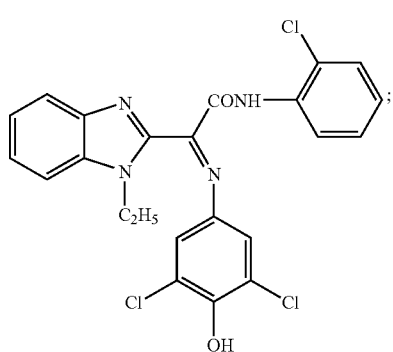
D-33
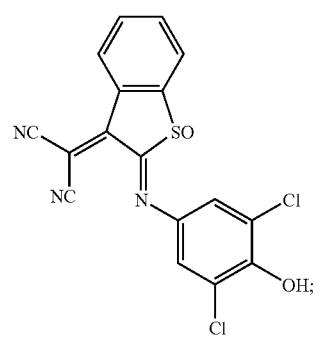
D-34
-continued
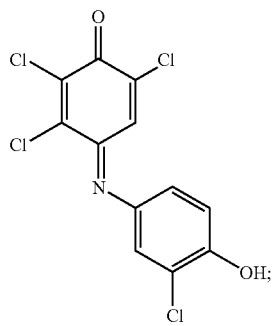
D-35
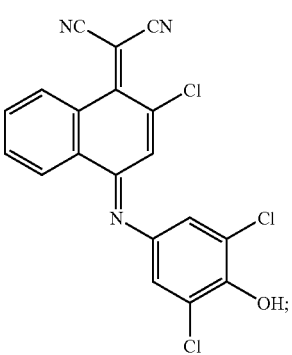
D-36
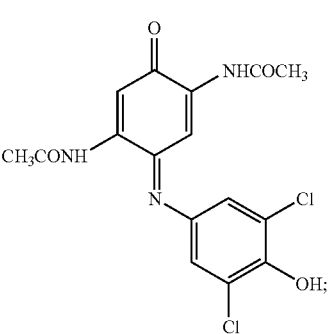
D-37
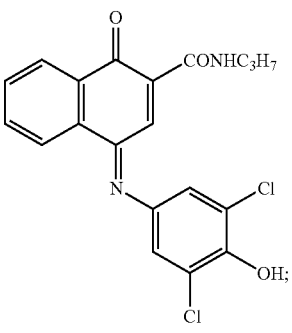
D-38
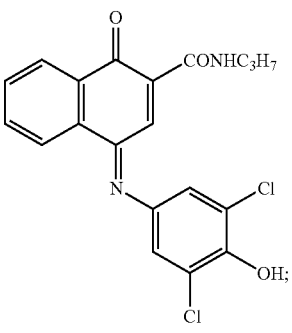
D-39

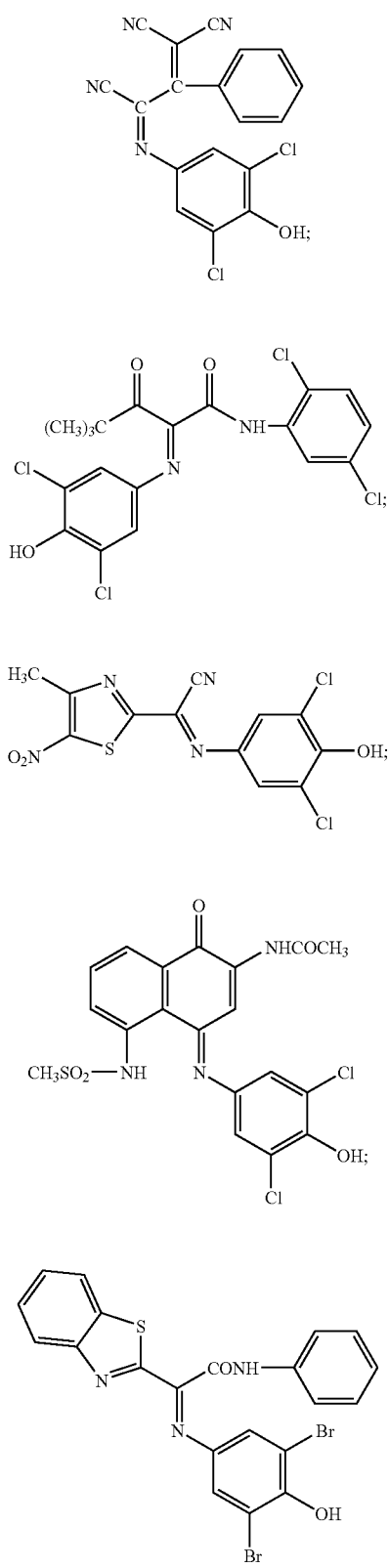
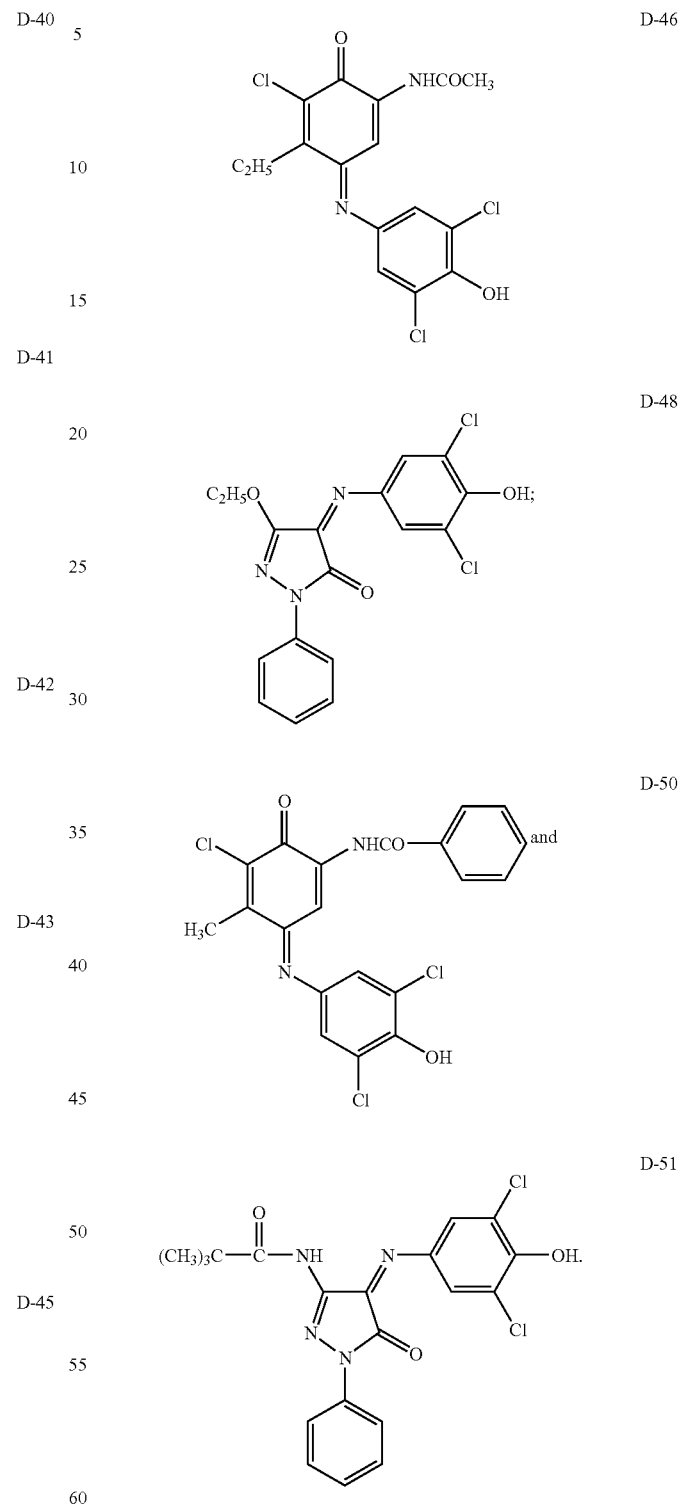
12. The hair dye composition of claim 1, further comprising at least one direct dye or oxidation dye.

13. The hair dye composition of claim 12, wherein the total amount of said dissociative direct dye and said at least one direct dye ranges from 0.001 to 20 wt. % based on the whole composition.

14. The hair dye composition of claim 1, wherein the pKa of said dissociative direct dye ranges from 1.5 to 9.

15. The hair dye composition of claim 1, wherein the amount of said dissociative direct dye ranges from 0.001 to 20 wt. % based on the whole composition.

16. The hair dye composition of claim 1, further comprising at least one additional component selected from the group consisting of an alkali agent, an oxidizing agent, a developer, a coupler, an oxidation dye, an autooxidation dye, a direct dye, a polyol, a polyol alkyl ether, a cationic polymer, an amphoteric polymer, a silicone, a hydrocarbon, an animal fat or oil, a vegetable fat or oil, a higher fatty acid, an organic solvent, a penetration promoter, a cationic surfactant, a natural polymer, a synthetic polymer, a higher alcohol, an ether, an amphoteric surfactant, a nonionic surfactant, an anionic surfactant, a protein derivative, an amino acid, an antiseptic, a chelating agent, a stabilizer, an antioxidant, a plant extract, a crude drug extract, a vitamin, a colorant, a perfume, and an ultraviolet absorber.

17. The hair dye composition of claim 1, wherein said hair dye composition is in a form selected from the group consisting of a powder, a transparent liquid, an emulsion, a cream, a gel, a paste, an aerosol, and an aerosol foam.

18. A method of dying hair, comprising applying to the hair of a subject in need thereof the hair dye composition of claim 1;

reacting said hair dye composition with said hair; and removing said hair dye composition from said hair.

19. A hair dye composition comprising a dissociative direct dye selected from the group consisting of

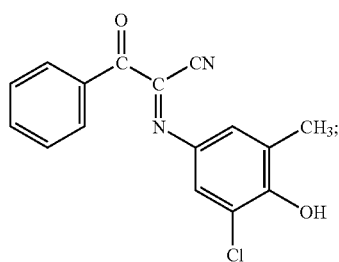

D-5

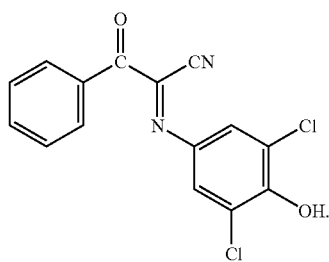

D-47

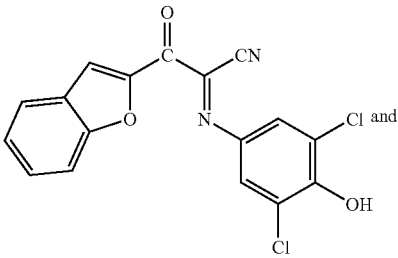

D-52

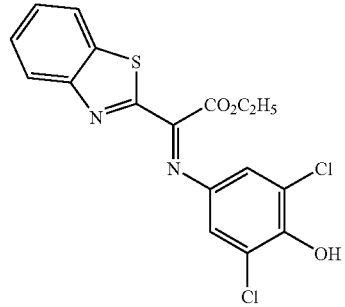

D-49 or a salt thereof.

20. The hair dye composition of claim 19, further comprising at least one direct dye or oxidation dye.

21. The hair dye composition of claim 20, wherein the total amount of said dissociative direct dye and said at least one direct dye ranges from 0.001 to 20 wt. % based on the whole composition.

22. The hair dye composition of claim 19, wherein the pKa of said dissociative direct dye ranges from 1.5 to 9.

23. The hair dye composition of claim 19, wherein the amount of said dissociative direct dye ranges from 0.001 to 20 wt. % based on the whole composition.

24. The hair dye composition of claim 19, further comprising at least one additional component selected from the group consisting of an alkali agent, an oxidizing agent, a developer, a coupler, an oxidation dye, an autooxidation dye, a direct dye, a polyol, a polyol alkyl ether, a cationic polymer, an amphoteric polymer, a silicone, a hydrocarbon, an animal fat or oil, a vegetable fat or oil, a higher fatty acid, an organic solvent, a penetration promoter, a cationic surfactant, a natural polymer, a synthetic polymer, a higher alcohol, an ether, an amphoteric surfactant, a nonionic surfactant, an anionic surfactant, a protein derivative, an amino acid, an antiseptic, a chelating agent, a stabilizer, an antioxidant, a plant extract, a crude drug extract, a vitamin, a colorant, a perfume, and an ultraviolet absorber.

25. The hair dye composition of claim 19, wherein said hair dye composition is in a form selected from the group consisting of a powder, a transparent liquid, an emulsion, a cream, a gel, a paste, an aerosol, and an aerosol foam.

26. A method of dying hair, comprising applying to the hair of a subject in need thereof the hair dye composition of claim 19;

reacting said hair dye composition with said hair; and removing said hair dye composition from said hair.

* * * * *